US012802812B2

(12) United States Patent
Neitzell et al.

(10) Patent No.: US 12,802,812 B2
(45) Date of Patent: Nov. 17, 2026

(54) RESPONSE BY ROBOTIC DEVICE TO AN ACUTE HEALTH EVENT REPORTED BY MEDICAL DEVICE

(71) Applicant: Medtronic, Inc., Minneapolis, MN (US)

(72) Inventors: Grant A. Neitzell, Loretto, MN (US); Shantanu Sarkar, Roseville, MN (US); Paul G. Krause, Mahtomedi, MN (US); Yong K. Cho, Excelsior, MN (US); Kevin T. Ousdigian, Shoreview, MN (US); Ryan D. Wyszynski, Oak Grove, MN (US); Christopher D. Koch, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 71 days.

(21) Appl. No.: 18/551,322

(22) PCT Filed: Feb. 17, 2022

(86) PCT No.: PCT/US2022/016679

§ 371 (c)(1),
(2) Date: Sep. 19, 2023

(87) PCT Pub. No.: WO2022/231678

PCT Pub. Date: Nov. 3, 2022

(65) Prior Publication Data

US 2024/0312623 A1 Sep. 19, 2024

Related U.S. Application Data

(60) Provisional application No. 63/182,482, filed on Apr. 30, 2021.

(51) Int. Cl.
*A61B 5/00* (2006.01)
*B25J 11/00* (2006.01)
(Continued)

(52) U.S. Cl.
CPC ............ *G16H 40/67* (2018.01); *B25J 11/009* (2013.01); *B25J 19/02* (2013.01)

(58) Field of Classification Search
CPC ........ G16H 40/67; G16H 10/20; G16H 10/60; G16H 20/17; G16H 40/63; G16H 50/20;
(Continued)

(56) References Cited

U.S. PATENT DOCUMENTS

| | | |
|---|---|---|
| 3,552,386 A | 1/1971 | Horth |
| 3,598,110 A | 8/1971 | Edmark |

(Continued)

FOREIGN PATENT DOCUMENTS

| | | |
|---|---|---|
| CA | 3075015 A1 | 9/2021 |
| CN | 105068486 A | 11/2015 |

(Continued)

OTHER PUBLICATIONS

"Cardiac Arrest: An Important Public Health Issue," CDC, retrieved from https://www.cdc.gov/dhdsp/docs/cardiac-arrest-infographic.pdf, on Apr. 23, 2021, 2 pp.

(Continued)

*Primary Examiner* — Masud Ahmed
(74) *Attorney, Agent, or Firm* — Shumaker & Sieffert, P.A.

(57) ABSTRACT

A device comprising a computer-readable medium having executable instructions stored thereon, configured to be executable by processing circuitry for causing the processing circuitry to: determine that a patient is experiencing or has experienced an acute health event; cause a motor to move a robotic device to a location proximate the patient; cause a sensor of the robotic device to gather physiological data from the patient; confirm that the patient is experiencing or has experienced the acute health event based on the physiological data; and generate an output in response to
(Continued)

confirming that the patient is experiencing or has experienced the acute health event.

24 Claims, 8 Drawing Sheets

(51) Int. Cl.
*B25J 19/02* (2006.01)
*G16H 40/67* (2018.01)

(58) Field of Classification Search
CPC ....... G16H 50/70; G16H 80/00; B25J 11/009; B25J 19/02; A61B 5/02455; A61B 5/33; A61B 5/7267; A61B 5/747; A61B 5/01; A61B 5/021; A61B 5/02405; A61B 5/0816; A61B 5/14542; A61B 5/4812; A61B 5/4836; A61B 5/686; A61B 5/7282; A61B 5/7221; A61B 5/746
See application file for complete search history.

(56) References Cited

U.S. PATENT DOCUMENTS

| | | | |
|---|---|---|---|
| 3,658,055 | A | 4/1972 | Abe et al. |
| 3,677,260 | A | 7/1972 | Funfstuck et al. |
| 3,828,768 | A | 8/1974 | Douglas |
| 3,861,387 | A | 1/1975 | Lawhorn et al. |
| 3,927,663 | A | 12/1975 | Russell et al. |
| 4,023,564 | A | 5/1977 | Valiquette et al. |
| 4,306,567 | A | 12/1981 | Krasner |
| 4,457,315 | A | 7/1984 | Bennish |
| 4,958,641 | A | 9/1990 | Digby et al. |
| 5,065,766 | A | 11/1991 | Sasaki |
| 5,217,021 | A | 6/1993 | Steinhaus et al. |
| 5,228,449 | A | 7/1993 | Christ et al. |
| 5,271,411 | A | 12/1993 | Ripley et al. |
| 5,366,487 | A | 11/1994 | Adams et al. |
| 5,404,877 | A | 4/1995 | Nolan et al. |
| 5,416,695 | A | 5/1995 | Stutman et al. |
| 5,458,123 | A | 10/1995 | Unger |
| 5,944,680 | A | 8/1999 | Christopherson et al. |
| 6,095,984 | A | 8/2000 | Amana et al. |
| 6,129,678 | A | 10/2000 | Ryan et al. |
| 6,292,687 | B1 | 9/2001 | Lowell et al. |
| 6,485,429 | B2 | 11/2002 | Forstner |
| 6,487,442 | B1 | 11/2002 | Wood |
| 6,490,478 | B1 | 12/2002 | Zhang et al. |
| 6,493,581 | B2 | 12/2002 | Russell |
| 6,609,023 | B1 | 8/2003 | Fischell et al. |
| 6,907,238 | B2 | 6/2005 | Leung |
| 6,980,112 | B2 | 12/2005 | Nee |
| 7,076,290 | B2 | 7/2006 | Sheth et al. |
| 7,092,751 | B2 | 8/2006 | Erkkili |
| 7,117,031 | B2 | 10/2006 | Lohman et al. |
| 7,194,354 | B1 | 3/2007 | Oran et al. |
| 7,212,849 | B2 | 5/2007 | Zhang et al. |
| 7,312,709 | B2 | 12/2007 | Kingston |
| 7,343,199 | B2 | 3/2008 | Hatlestad et al. |
| 7,353,179 | B2 | 4/2008 | Ott et al. |
| 7,396,330 | B2 | 7/2008 | Banet et al. |
| 7,480,529 | B2 | 1/2009 | Li |
| 7,502,498 | B2 | 3/2009 | Wen et al. |
| 7,558,623 | B2 | 7/2009 | Fischell et al. |
| 7,689,282 | B2 | 3/2010 | Zhang et al. |
| 7,702,382 | B2 | 4/2010 | Xue |
| 7,715,905 | B2 | 5/2010 | Kurzweil et al. |
| 7,733,224 | B2 | 6/2010 | Tran |
| 7,801,596 | B2 | 9/2010 | Fischell et al. |
| 7,840,277 | B2 | 11/2010 | Matos |
| 7,844,323 | B2 | 11/2010 | Fischell et al. |
| 7,846,106 | B2 | 12/2010 | Andrews et al. |
| 7,860,559 | B2 | 12/2010 | Fischell et al. |
| 7,889,092 | B2 | 2/2011 | Volk et al. |
| 7,894,883 | B2 | 2/2011 | Gunderson et al. |
| 7,991,460 | B2 | 8/2011 | Fischell et al. |
| 8,002,701 | B2 | 8/2011 | John et al. |
| 8,073,536 | B2 | 12/2011 | Gunderson et al. |
| 8,073,537 | B2 | 12/2011 | Gunderson et al. |
| 8,108,036 | B2 | 1/2012 | Tran |
| 8,112,153 | B2 | 2/2012 | Giftakis et al. |
| 8,170,609 | B2 | 5/2012 | Hedtke et al. |
| 8,170,653 | B2 | 5/2012 | Fischell et al. |
| 8,204,580 | B2 | 6/2012 | Kurzweil et al. |
| 8,214,043 | B2 | 7/2012 | Matos |
| 8,224,430 | B2 | 7/2012 | Fischell et al. |
| 8,239,020 | B2 | 8/2012 | Zhang et al. |
| 8,265,740 | B2 | 9/2012 | Fischell et al. |
| 8,265,751 | B2 | 9/2012 | Zhang et al. |
| 8,275,457 | B1 | 9/2012 | Fischell et al. |
| 8,301,236 | B2 | 10/2012 | Baumann et al. |
| 8,323,189 | B2 | 12/2012 | Tran et al. |
| 8,332,233 | B2 | 12/2012 | Ott et al. |
| 8,352,018 | B2 | 1/2013 | Xue |
| 8,369,936 | B2 | 2/2013 | Farringdon et al. |
| 8,401,644 | B2 | 3/2013 | Gunderson et al. |
| 8,423,128 | B2 | 4/2013 | Goto |
| 8,433,399 | B1 | 4/2013 | Nosrati et al. |
| 8,437,840 | B2 | 5/2013 | Patel et al. |
| 8,461,988 | B2 | 6/2013 | Tran |
| 8,473,065 | B2 | 6/2013 | Matos |
| 8,483,807 | B2 | 7/2013 | Kurzweil et al. |
| 8,512,257 | B2 | 8/2013 | Fischell et al. |
| 8,521,281 | B2 | 8/2013 | Patel et al. |
| 8,525,673 | B2 | 9/2013 | Tran |
| 8,525,687 | B2 | 9/2013 | Tran |
| 8,531,291 | B2 | 9/2013 | Tran |
| 8,554,315 | B2 | 10/2013 | Cho et al. |
| 8,560,069 | B2 | 10/2013 | Zhang |
| 8,562,524 | B2 | 10/2013 | Osorio |
| 8,565,882 | B2 | 10/2013 | Matos |
| 8,583,251 | B2 | 11/2013 | Matos |
| 8,630,702 | B2 | 1/2014 | Fischell et al. |
| 8,680,991 | B2 | 3/2014 | Tran |
| 8,682,284 | B2 | 3/2014 | Brackett et al. |
| 8,684,922 | B2 | 4/2014 | Tran |
| 8,706,217 | B2 | 4/2014 | Bardy et al. |
| 8,706,225 | B2 | 4/2014 | Matos |
| 8,712,509 | B2 | 4/2014 | Lee et al. |
| 8,718,752 | B2 | 5/2014 | Libbus et al. |
| 8,738,120 | B2 | 5/2014 | Björling et al. |
| 8,747,336 | B2 | 6/2014 | Tran |
| 8,774,908 | B2 | 7/2014 | Stewart |
| 8,774,909 | B2 | 7/2014 | Patel et al. |
| 8,805,529 | B2 | 8/2014 | Matos |
| 8,825,146 | B2 | 9/2014 | Li |
| 8,831,725 | B2 | 9/2014 | Gunderson et al. |
| 8,849,400 | B2 | 9/2014 | Gunderson et al. |
| 8,855,550 | B2 | 10/2014 | Gaines et al. |
| 8,862,393 | B2 | 10/2014 | Zhou et al. |
| 8,886,296 | B2 | 11/2014 | Patel |
| 8,909,332 | B2 | 12/2014 | Vitali et al. |
| 8,923,960 | B2 | 12/2014 | Goto |
| 8,954,137 | B2 | 2/2015 | Kurzweil et al. |
| 8,965,494 | B2 | 2/2015 | Fischell et al. |
| 8,983,587 | B2 | 3/2015 | Kurzweil et al. |
| 8,983,682 | B1 | 3/2015 | Peeters et al. |
| 9,028,405 | B2 | 5/2015 | Tran |
| 9,031,645 | B2 | 5/2015 | Houben et al. |
| 9,044,148 | B2 | 6/2015 | Michaelson et al. |
| 9,060,746 | B2 | 6/2015 | Weng et al. |
| 9,082,156 | B2 | 7/2015 | Matos |
| 9,095,727 | B2 | 8/2015 | Matos |
| 9,101,278 | B2 | 8/2015 | Fischell et al. |
| 9,113,830 | B2 | 8/2015 | Galen et al. |
| 9,138,590 | B2 | 9/2015 | Zhang et al. |
| 9,179,255 | B2 | 11/2015 | Stephens et al. |
| 9,179,851 | B2 | 11/2015 | Baumann et al. |
| 9,204,796 | B2 | 12/2015 | Tran |
| 9,237,243 | B2 | 1/2016 | Jensen et al. |
| 9,241,677 | B2 | 1/2016 | Liao-Chen et al. |
| 9,254,092 | B2 | 2/2016 | Albert et al. |
| 9,293,025 | B2 | 3/2016 | Zhang |
| 9,307,383 | B1 | 4/2016 | Patrick |

(56) References Cited

U.S. PATENT DOCUMENTS

| | | | | |
|---|---|---|---|---|
| 9,314,181 | B2 | 4/2016 | Brockway et al. | |
| 9,351,640 | B2 | 5/2016 | Tran | |
| 9,364,158 | B2 | 6/2016 | Banet et al. | |
| 9,445,736 | B2 | 9/2016 | Kurzweil et al. | |
| 9,456,787 | B2 | 10/2016 | Venkatraman et al. | |
| 9,468,383 | B2 | 10/2016 | Fischell et al. | |
| 9,491,277 | B2 | 11/2016 | Vincent | |
| 9,498,152 | B2 | 11/2016 | Bowers | |
| 9,642,167 | B1 | 5/2017 | Snyder et al. | |
| 9,662,015 | B2 | 5/2017 | Proud et al. | |
| 9,668,665 | B2 | 6/2017 | Schroeder et al. | |
| 9,681,814 | B2 | 6/2017 | Galloway et al. | |
| 9,724,008 | B2 * | 8/2017 | Sullivan | A61N 1/3925 |
| 9,724,046 | B2 | 8/2017 | Forstner | |
| 9,730,604 | B2 | 8/2017 | Li et al. | |
| 9,735,896 | B2 | 8/2017 | Flippo et al. | |
| 9,770,181 | B2 | 9/2017 | Kurzweil et al. | |
| 9,775,520 | B2 | 10/2017 | Tran | |
| 9,820,667 | B2 | 11/2017 | Ting et al. | |
| 9,824,188 | B2 | 11/2017 | Brown et al. | |
| 9,826,358 | B2 | 11/2017 | Ryan et al. | |
| 9,852,599 | B1 | 12/2017 | Slavin et al. | |
| 9,855,434 | B2 | 1/2018 | Matos | |
| 9,901,252 | B2 | 2/2018 | Tran | |
| 9,913,583 | B2 | 3/2018 | Smith, Sr. | |
| 9,979,810 | B2 | 5/2018 | Mazar et al. | |
| 9,997,055 | B2 | 6/2018 | Ball | |
| 10,003,394 | B2 | 6/2018 | Bromberg et al. | |
| 10,039,469 | B2 | 8/2018 | Higgins et al. | |
| 10,044,857 | B2 | 8/2018 | Philbin | |
| 10,085,115 | B2 | 9/2018 | Mayor et al. | |
| 10,098,561 | B2 | 10/2018 | Brockway et al. | |
| 10,117,595 | B2 | 11/2018 | Chang et al. | |
| 10,117,606 | B2 | 11/2018 | Feldman et al. | |
| 10,123,741 | B2 | 11/2018 | Wang et al. | |
| 10,136,826 | B2 | 11/2018 | Sullivan et al. | |
| 10,165,400 | B2 | 12/2018 | Raj | |
| 10,201,710 | B2 | 2/2019 | Jackson et al. | |
| 10,206,593 | B2 | 2/2019 | Ukil et al. | |
| 10,272,010 | B2 | 4/2019 | Freeman et al. | |
| 10,278,050 | B2 | 4/2019 | Winkler et al. | |
| 10,278,607 | B2 | 5/2019 | Prystowsky et al. | |
| 10,307,060 | B2 | 6/2019 | Tran | |
| 10,362,940 | B2 | 7/2019 | Tran | |
| 10,368,807 | B2 | 8/2019 | Melker et al. | |
| 10,375,558 | B2 | 8/2019 | Katz et al. | |
| 10,420,529 | B2 | 9/2019 | Wang et al. | |
| 10,463,295 | B2 | 11/2019 | Zhou | |
| 10,492,686 | B2 | 12/2019 | Hunter et al. | |
| 10,493,290 | B2 | 12/2019 | Ludwig et al. | |
| 10,517,479 | B2 | 12/2019 | Tran | |
| 10,524,736 | B2 | 1/2020 | Gross | |
| 10,531,266 | B2 | 1/2020 | Rauner et al. | |
| 10,537,263 | B2 | 1/2020 | Ibáñez Català | |
| 10,540,878 | B2 | 1/2020 | Hunter et al. | |
| 10,575,748 | B2 | 3/2020 | Higgins et al. | |
| 10,595,731 | B2 | 3/2020 | Gopalakrishnan et al. | |
| 10,602,942 | B2 | 3/2020 | Shakur et al. | |
| 10,616,664 | B2 | 4/2020 | Alman et al. | |
| 10,616,747 | B2 | 4/2020 | Piett et al. | |
| 10,617,356 | B2 | 4/2020 | Wang et al. | |
| 10,624,550 | B2 | 4/2020 | Soli et al. | |
| 10,631,742 | B2 | 4/2020 | Tal et al. | |
| 10,631,744 | B2 | 4/2020 | Mahajan et al. | |
| 10,657,796 | B2 | 5/2020 | Bowers | |
| 10,674,342 | B2 | 6/2020 | Park et al. | |
| 10,702,213 | B2 | 7/2020 | Sharma et al. | |
| 10,736,532 | B2 | 8/2020 | Bardy et al. | |
| 10,758,140 | B2 | 9/2020 | Kurzweil et al. | |
| 10,796,552 | B2 | 10/2020 | Fahey | |
| 10,814,978 | B2 | 10/2020 | Walker et al. | |
| 10,882,180 | B2 | 1/2021 | Wright et al. | |
| 10,888,705 | B2 | 1/2021 | Matos | |
| 10,905,328 | B2 | 2/2021 | Murphy et al. | |
| 10,981,009 | B2 | 4/2021 | Jackson et al. | |
| 11,024,432 | B2 | 6/2021 | Chiu et al. | |
| 11,064,339 | B2 | 7/2021 | Hamre et al. | |
| 11,103,176 | B2 | 8/2021 | Galloway et al. | |
| 11,103,194 | B2 | 8/2021 | Galloway et al. | |
| 11,116,448 | B1 | 9/2021 | Trapero Martin et al. | |
| 11,116,989 | B2 | 9/2021 | Gill et al. | |
| 11,160,484 | B2 | 11/2021 | Sullivan et al. | |
| 11,197,629 | B2 | 12/2021 | Remes et al. | |
| 11,198,017 | B2 | 12/2021 | Kaib et al. | |
| 11,202,174 | B2 | 12/2021 | Klinkner et al. | |
| 11,218,584 | B2 | 1/2022 | Martin et al. | |
| 11,219,373 | B2 | 1/2022 | Eggers et al. | |
| 11,228,891 | B2 | 1/2022 | King-Berkman et al. | |
| 11,230,242 | B2 | 1/2022 | Makled et al. | |
| 11,234,604 | B2 | 2/2022 | Albert | |
| 11,235,143 | B2 | 2/2022 | Medema et al. | |
| 11,278,201 | B2 | 3/2022 | Thomson et al. | |
| 11,289,197 | B1 | 3/2022 | Park et al. | |
| 11,291,401 | B2 | 4/2022 | Velo | |
| 11,309,083 | B2 * | 4/2022 | Costantino | G06Q 30/0185 |
| 11,311,230 | B2 | 4/2022 | Sullivan et al. | |
| 11,331,475 | B2 | 5/2022 | Drake et al. | |
| 11,341,839 | B2 | 5/2022 | Cruver et al. | |
| 11,344,244 | B2 | 5/2022 | Albert | |
| 11,363,952 | B2 | 6/2022 | Venkatraman et al. | |
| 11,406,314 | B2 | 8/2022 | Henry et al. | |
| 11,623,102 | B2 | 4/2023 | Schulhauser et al. | |
| 11,633,112 | B2 | 4/2023 | Stadler et al. | |
| 11,657,910 | B2 | 5/2023 | Halsne et al. | |
| 11,679,268 | B2 | 6/2023 | Haddad et al. | |
| 11,684,776 | B2 | 6/2023 | Grubac et al. | |
| 12,142,351 | B2 * | 11/2024 | Pinter | A61B 5/165 |
| 2002/0032383 | A1 | 3/2002 | Weil et al. | |
| 2003/0023175 | A1 | 1/2003 | Arzbaecher et al. | |
| 2003/0176798 | A1 | 9/2003 | Simon | |
| 2003/0191402 | A1 | 10/2003 | Arzbaecher et al. | |
| 2003/0212311 | A1 | 11/2003 | Nova et al. | |
| 2003/0214409 | A1 | 11/2003 | Hickle | |
| 2003/0233129 | A1 | 12/2003 | Matos | |
| 2004/0172069 | A1 | 9/2004 | Hakala | |
| 2004/0199212 | A1 | 10/2004 | Fischell et al. | |
| 2005/0065445 | A1 | 3/2005 | Arzbaecher et al. | |
| 2005/0154325 | A1 | 7/2005 | Lauter et al. | |
| 2005/0228305 | A1 | 10/2005 | Nagata et al. | |
| 2005/0234313 | A1 | 10/2005 | Rowlandson et al. | |
| 2006/0030781 | A1 | 2/2006 | Shennib | |
| 2006/0155206 | A1 | 7/2006 | Lynn | |
| 2006/0173498 | A1 | 8/2006 | Banville et al. | |
| 2006/0264767 | A1 | 11/2006 | Shennib | |
| 2006/0284732 | A1 | 12/2006 | Brock-Fisher | |
| 2007/0043585 | A1 | 2/2007 | Matos | |
| 2007/0049976 | A1 | 3/2007 | Ni et al. | |
| 2007/0249944 | A1 | 10/2007 | Fischell et al. | |
| 2007/0260285 | A1 | 11/2007 | Libbus et al. | |
| 2007/0260289 | A1 | 11/2007 | Giftakis et al. | |
| 2007/0293775 | A1 | 12/2007 | Fischell et al. | |
| 2007/0299473 | A1 | 12/2007 | Matos | |
| 2008/0058660 | A1 | 3/2008 | Fischell et al. | |
| 2008/0064973 | A1 | 3/2008 | Fischell et al. | |
| 2008/0139954 | A1 | 6/2008 | Day et al. | |
| 2008/0177194 | A1 | 7/2008 | Zhang et al. | |
| 2008/0270036 | A1 | 10/2008 | Webb | |
| 2009/0054027 | A1 | 2/2009 | Jenkins | |
| 2009/0062670 | A1 | 3/2009 | Sterling et al. | |
| 2009/0076559 | A1 | 3/2009 | Libbus et al. | |
| 2009/0149849 | A1 | 6/2009 | Lin et al. | |
| 2009/0240156 | A1 | 9/2009 | Fischell et al. | |
| 2009/0322513 | A1 | 12/2009 | Hwang et al. | |
| 2009/0326595 | A1 | 12/2009 | Brockway et al. | |
| 2010/0016746 | A1 | 1/2010 | Hampton et al. | |
| 2010/0022902 | A1 | 1/2010 | Lee et al. | |
| 2010/0286490 | A1 | 11/2010 | Koverzin et al. | |
| 2011/0054934 | A1 | 3/2011 | Vesto | |
| 2011/0105928 | A1 | 5/2011 | Bojovic et al. | |
| 2011/0112417 | A1 | 5/2011 | Gunderson et al. | |
| 2011/0193704 | A1 | 8/2011 | Harper et al. | |
| 2011/0230161 | A1 | 9/2011 | Newman | |
| 2011/0288417 | A1 * | 11/2011 | Pinter | G16Z 99/00 600/595 |

(56) References Cited

U.S. PATENT DOCUMENTS

2012/0190969 A1 7/2012 Kameli
2012/0191150 A1 7/2012 Kameli
2012/0191151 A1 7/2012 Kameli
2012/0191152 A1 7/2012 Kameli
2012/0220835 A1 8/2012 Chung
2012/0242501 A1 9/2012 Tran et al.
2012/0306652 A1 12/2012 Musol et al.
2012/0330171 A1 12/2012 Zhang et al.
2013/0095459 A1 4/2013 Tran
2013/0211291 A1 8/2013 Tran
2013/0245466 A1 9/2013 Sachanandani et al.
2014/0100497 A1 4/2014 Hayashi et al.
2014/0139616 A1 5/2014 Pinter
2014/0152436 A1 6/2014 Langer
2014/0163425 A1 6/2014 Tran
2014/0213202 A1 7/2014 Wang et al.
2014/0293053 A1 10/2014 Chuang
2015/0018658 A1 1/2015 Fischell et al.
2015/0045868 A1 2/2015 Bonner et al.
2015/0105632 A1 4/2015 Melker et al.
2015/0112605 A1 4/2015 Watson et al.
2015/0118658 A1 4/2015 Mayou et al.
2015/0158988 A1 6/2015 Sawaki et al.
2015/0164375 A1 6/2015 Schindhelm et al.
2015/0173689 A1 6/2015 Owen et al.
2015/0223759 A1 8/2015 Ong et al.
2015/0302539 A1 10/2015 Mazar et al.
2015/0366518 A1 12/2015 Sampson
2016/0000349 A1 1/2016 Sullivan et al.
2016/0008614 A1 1/2016 Zhang et al.
2016/0035204 A1 2/2016 Jansen
2016/0106378 A1 4/2016 Kyal et al.
2016/0120434 A1 5/2016 Park et al.
2016/0128595 A1 5/2016 Fischell et al.
2016/0135706 A1* 5/2016 Sullivan ............... A61B 5/7275
600/509
2016/0151021 A1 6/2016 Feng et al.
2016/0174857 A1 6/2016 Eggers et al.
2016/0174875 A1 6/2016 Forster et al.
2016/0325107 A1 11/2016 Park et al.
2016/0328950 A1 11/2016 Pelletier et al.
2016/0331330 A1 11/2016 Freeman et al.
2016/0354011 A1 12/2016 Stahl
2017/0007167 A1 1/2017 Kostic et al.
2017/0083667 A1 3/2017 Darrah et al.
2017/0099579 A1 4/2017 Ryan et al.
2017/0202463 A1 7/2017 Muhksteff et al.
2017/0246329 A1 8/2017 Lloyd
2017/0281097 A1 10/2017 Thakur et al.
2017/0296076 A1 10/2017 Mahajan et al.
2017/0323485 A1 11/2017 Samec et al.
2017/0330438 A1 11/2017 Howard et al.
2017/0337339 A1 11/2017 Cronin et al.
2017/0354365 A1 12/2017 Zhou
2017/0360361 A1 12/2017 Long et al.
2017/0366921 A1 12/2017 Pflugh et al.
2018/0008159 A1 1/2018 Wang et al.
2018/0008797 A1 1/2018 Kozloski et al.
2018/0091657 A1 3/2018 Brown et al.
2018/0113986 A1 4/2018 Zhu
2018/0113987 A1 4/2018 Zhu
2018/0116537 A1 5/2018 Sullivan et al.
2018/0117299 A1 5/2018 Gustavson et al.
2018/0146922 A1 5/2018 Wang et al.
2018/0192894 A1 7/2018 An et al.
2018/0220897 A1 8/2018 Meger et al.
2018/0221645 A1 8/2018 Medema et al.
2018/0235537 A1 8/2018 Whiting et al.
2018/0243578 A1 8/2018 Volosin
2018/0247713 A1 8/2018 Rothman et al.
2018/0260706 A1 9/2018 Galloway et al.
2018/0301017 A1 10/2018 Dizengof et al.
2018/0322405 A1 11/2018 Fadell et al.
2018/0338731 A1 11/2018 Addison et al.
2018/0348759 A1 12/2018 Freeman et al.
2019/0043616 A1 2/2019 Howard et al.
2019/0066538 A1 2/2019 Chao et al.
2019/0083804 A1 3/2019 Grinberg et al.
2019/0125273 A1 5/2019 Sharma et al.
2019/0197861 A1 6/2019 Tunnell et al.
2019/0275225 A1 9/2019 Brown
2019/0279480 A1 9/2019 Lee et al.
2019/0290216 A1 9/2019 Koyama
2019/0298201 A1 10/2019 Persen et al.
2019/0307328 A1 10/2019 Tran
2019/0328251 A1 10/2019 Jin
2019/0336767 A1 11/2019 Klepfer et al.
2019/0358820 A1 11/2019 Wojciechowski et al.
2019/0365264 A1 12/2019 Freeman et al.
2019/0365269 A1 12/2019 Jun
2019/0391581 A1 12/2019 Vardaro et al.
2020/0008696 A1 1/2020 Sirendi et al.
2020/0038671 A1 2/2020 Schulhauser et al.
2020/0046241 A1 2/2020 Lam et al.
2020/0069245 A1 3/2020 Zhou
2020/0077892 A1 3/2020 Tran
2020/0085380 A1 3/2020 Sampson
2020/0100693 A1 4/2020 Velo
2020/0113459 A1 4/2020 Jäntti et al.
2020/0146550 A1 5/2020 Tunnell et al.
2020/0146930 A1 5/2020 Freeman et al.
2020/0160991 A1 5/2020 Smith et al.
2020/0178821 A1 6/2020 Wu et al.
2020/0197706 A1 6/2020 Grenz et al.
2020/0305737 A1 10/2020 Tseng et al.
2020/0306530 A1 10/2020 Koop et al.
2020/0337567 A1 10/2020 McCalmont et al.
2020/0337581 A1 10/2020 Jung et al.
2020/0338356 A1 10/2020 Anderson et al.
2020/0342966 A1 10/2020 Stern et al.
2020/0346751 A1 11/2020 Horelik et al.
2020/0352462 A1 11/2020 Pedalty et al.
2020/0352466 A1 11/2020 Chakravarthy et al.
2020/0352522 A1 11/2020 Chakravarthy et al.
2020/0357519 A1 11/2020 Chakravarthy et al.
2020/0373005 A1 11/2020 Halsne et al.
2020/0380840 A1 12/2020 Galarneau et al.
2020/0390354 A1 12/2020 Huegerich et al.
2020/0397308 A1 12/2020 Sarkar et al.
2021/0046306 A1 2/2021 Grubac et al.
2021/0069491 A1 3/2021 Grubac et al.
2021/0118562 A1 4/2021 Matos
2021/0121090 A1 4/2021 Weinstein et al.
2021/0138243 A1 5/2021 Zhang et al.
2021/0138254 A1 5/2021 Matos
2021/0154477 A1 5/2021 Asleson et al.
2021/0154487 A1 5/2021 Bongberg et al.
2021/0169392 A1 6/2021 Albert et al.
2021/0186329 A1* 6/2021 Tran ....................... A61B 5/002
2021/0236814 A1 8/2021 Anderson et al.
2021/0251578 A1 8/2021 Schulhauser et al.
2021/0259560 A1 8/2021 Venkatraman et al.
2021/0275824 A1 9/2021 Rock et al.
2021/0314756 A1 10/2021 Brooks et al.
2021/0338134 A1 11/2021 Chakravarthy et al.
2021/0338138 A1 11/2021 Pedalty et al.
2021/0343132 A1 11/2021 Bonser
2021/0343416 A1 11/2021 Chakravarthy et al.
2021/0345934 A1 11/2021 Landgraf et al.
2021/0353166 A1 11/2021 Sirendi et al.
2021/0394369 A1 12/2021 Oh et al.
2021/0401349 A1 12/2021 Schram
2022/0023626 A1 1/2022 Haddad et al.
2022/0031253 A1 2/2022 Burnes et al.
2022/0039729 A1 2/2022 Fontanarava et al.
2022/0051548 A1 2/2022 Pellegrini et al.
2022/0061678 A1 3/2022 Schulhauser et al.
2022/0062630 A1 3/2022 Yang et al.
2022/0095982 A1 3/2022 de Saint Victor et al.
2022/0151533 A1 5/2022 Moon
2022/0160250 A1 5/2022 Anderson et al.
2022/0183607 A1 6/2022 Volosin et al.
2022/0218259 A1 7/2022 Laversin et al.
2022/0249026 A1 8/2022 Heneghan et al.

(56) References Cited

U.S. PATENT DOCUMENTS

| | | | |
|---|---|---|---|
| 2022/0265997 A1 | 8/2022 | Drake et al. |
| 2022/0280047 A1 | 9/2022 | Stadler et al. |
| 2022/0346725 A1 | 11/2022 | Krause et al. |
| 2022/0369937 A1 | 11/2022 | Cho et al. |
| 2023/0263406 A1 | 8/2023 | Stadler et al. |
| 2023/0271000 A1 | 8/2023 | Grubac et al. |
| 2024/0062856 A1 | 2/2024 | Haddad et al. |
| 2024/0312623 A1 | 9/2024 | Neitzell et al. |
| 2025/0114596 A1 | 4/2025 | Grubac et al. |

FOREIGN PATENT DOCUMENTS

| | | | |
|---|---|---|---|
| CN | 105769171 | A | 7/2016 |
| CN | 106264518 | A | 1/2017 |
| CN | 106562777 | A | 4/2017 |
| CN | 107874753 | A | 4/2018 |
| CN | 108039203 | A | 5/2018 |
| CN | 108324264 | A | 7/2018 |
| CN | 207924885 | U | 9/2018 |
| CN | 109009047 | A | 12/2018 |
| CN | 208460154 | U | 2/2019 |
| CN | 109820492 | A | 5/2019 |
| CN | 109953753 | A | 7/2019 |
| CN | 111667921 | A | 9/2020 |
| CN | 112022145 | A | 12/2020 |
| CN | 112515650 | A | 3/2021 |
| CN | 112515651 | A | 3/2021 |
| CN | 113080917 | A | 7/2021 |
| CN | 113598784 | A | 11/2021 |
| CN | 215128553 | U | 12/2021 |
| CN | 114711781 | A | 7/2022 |
| CN | 217014071 | U | 7/2022 |
| DE | 202019105583 | U1 | 11/2019 |
| EP | 2689363 | A2 | 1/2014 |
| ES | 2559263 | T3 | 2/2016 |
| FI | 128143 | B | 12/2018 |
| GB | 2569157 | A | 6/2019 |
| GB | 2590556 | B | 6/2021 |
| GB | 2600710 | A | 5/2022 |
| IN | 201811048444 | A | 12/2018 |
| JP | 3031277 | B2 | 4/2000 |
| JP | 2007289694 | A | 11/2007 |
| JP | 2009089883 | A | 4/2009 |
| JP | 2018500967 | A | 1/2018 |
| JP | 2018503885 | A | 2/2018 |
| JP | 2018122097 | A | 8/2018 |
| JP | 6764830 | A | 12/2018 |
| JP | 2019129954 | A | 8/2019 |
| JP | 2020515322 | A | 5/2020 |
| JP | 2020119422 | A | 8/2020 |
| KR | 20030008655 | A | 1/2003 |
| KR | 100400212 | B1 | 11/2003 |
| KR | 100637566 | B1 | 10/2006 |
| KR | 101756787 | B1 | 7/2017 |
| KR | 102195189 | B1 | 12/2020 |
| MX | 2016007079 | A | 11/2017 |
| SU | 442789 | A1 | 9/1974 |
| SU | 1042732 | A1 | 9/1983 |
| TR | 201719097 | A2 | 6/2019 |
| TW | M555707 | U | 2/2018 |
| TW | I669097 | B | 8/2019 |
| WO | 2005021089 | A1 | 3/2005 |
| WO | 2009001361 | A2 | 12/2008 |
| WO | 2010105053 | A3 | 1/2011 |
| WO | 2012135059 | A2 | 10/2012 |
| WO | 2016034203 | A1 | 3/2016 |
| WO | 2017059274 | A1 | 4/2017 |
| WO | 2018178358 | A1 | 10/2018 |
| WO | 2018202606 | A1 | 11/2018 |
| WO | 2019096876 | A1 | 5/2019 |
| WO | 2019110963 | A1 | 6/2019 |
| WO | 2020115747 | A1 | 6/2020 |
| WO | 2020141727 | A1 | 7/2020 |
| WO | 2020155078 | A1 | 8/2020 |
| WO | 2020226879 | | 11/2020 |
| WO | 2020226881 | | 11/2020 |
| WO | 2020226887 | | 11/2020 |
| WO | 2021084535 | | 5/2021 |
| WO | 2021133360 | A1 | 7/2021 |
| WO | 2021181389 | A1 | 9/2021 |
| WO | 2022034045 | | 2/2022 |
| WO | 2022034480 | | 2/2022 |
| WO | 2022070109 | | 4/2022 |
| WO | 2022130152 | | 6/2022 |
| WO | 2022173646 | A1 | 8/2022 |

OTHER PUBLICATIONS

"Heart Disease and Stroke Statistics—2019 Update a Report From the American Heart Association," Circulation, vol. 139, Mar. 5, 2019 pp. e56-e528.

"Highlights of the 2020 American Heart Association Guidelines for CPR and ECC," American Heart Association, 2020 (Applicant points out, in accordance with MPEP 609.04(a), that the year of publication, 2020, is sufficiently earlier than the effective U.S. filing date, so that the particular month of publication is not in issue.) 32 p.

"Monitor your heart rate with Apple Watch," retrieved from https://support.apple.com/en-us/HT204666, on Apr. 23, 2021, 8 pp.

"Protocol 9, Cardiac or Respiratory Arrest," The EMD Protocol, National Academy Medical Prioity Dispatch System, Accessed on Apr. 23, 2021, 5 pp.

"Using Apple Watch for Arrhythmia Detection," Apple, Inc., Dec. 2020, 17 pp.

Auer et al., "A Smartwatch to Identify Atrial Fibrillation," The New England Journal of Medicine, vol. 382, No. 10, Mar. 5, 2020, pp. 974-976.

Bayanbay et al., "The Use of Unmanned Aerial Vehicle for Emergency Medical Assistance," 2019 20th International Conference of Young Specialists on Micro/Nanotechnologies and Electron Devices (EDM), Jun. 29-Jul. 3, 2019, pp. 597-600.

Beauchamp et al., "The Use of Wearables in Clinical Trials During Cancer Treatment: Systematic Review," JMIR Mhealth Uhealth, vol. 8, No. 11, e22006, Nov. 2020, 15 pp.

Blomberg et al., "Effect of Machine Learning on Dispatcher Recognition of Out-of-Hospital Cardiac Arrest During Calls to Emergency Medical Services A Randomized Clinical Trial," JAMA Network Open, Jan. 6, 2021, 10 pp.

Book of Abstracts, Acta Cardiologica, vol. 76, supp 1, Feb. 22, 2021, 52 pp.

Bumgarner et al., "Smartwatch Algorithm for Automated Detection of Atrial Fibrillation," Journal of the American College of Cardiology, vol. 71, No. 21, May 29, 2018, pp. 2381-2388.

Burke et al., "Smartwatch Detection of Ventricular Tachycardia: Case Series," Heart Rhythm Case Reports, vol. 6, No. 10, Oct. 2020, pp. 801-804.

Campion et al., "Watched by Apple," The New England Journal of Medicine, vol. 381, No. 20, Nov. 14, 2019, pp. 1964-1965.

CARES Annual Report 2019, 2019 (Applicant points out, in accordance with MPEP 609.04(a), that the year of publication, 2019, is sufficiently earlier than the effective U.S. filing date, so that the particular month of publication is not in issue.) 48 pp.

Carpenter et al., "Smart-Watches: a Potential Challenger to the Implantable Loop Recorder?," Europace, vol. 18, Feb. 2016, pp. 791-793.

Centers for Disease Control and Prevention et al., "What is v-safe?", Jun. 10, 2022, 1 pp., URL: https://www.cdc.gov/coronavirus/2019-ncov/vaccines/safety/pdfs/v-safe- information-sheet-508c.pdf.

Chan et al., "Contactless Cardiac Arrest Detection Using Smart Devices," NPJ Digital Medicine, vol. 2, No. 52, Jun. 19, 2019, 8 pp.

Dayananda et al., "An Interconnected Architecture for an Emergency Medical Response Unmanned Aerial System," 2017 IEEE/AIAA 36th Digital Avionics Systems Conference (DASC), Sep. 17-21, 2017, pp. 1-6.

Deo et al., "Epidemiology and Genetics of Sudden Cardiac Death," Circulation, vol. 125, No. 4, Jan. 31, 2012, pp. 620-637.

(56) References Cited

OTHER PUBLICATIONS

Giancaterino et al., "The Smartwatch Will See You Now: Implications of Mass Screening for Atrial Fibrillation," Journal of the American College of Cardiology, vol. 72, No. 12, Sep. 18, 2018, pp. 1433-1434.
Goldberger et al., "Risk Stratification for Sudden Cardiac Death a Plan for the Future," Circulation, vol. 129, No. 4, Jan. 28, 2014, pp. 516-526.
Hause et al., "COVID-19 Vaccine Safety in Adolescents Aged 12-17 Years—United States, Dec. 14, 2020-Jul. 16, 2021", Centers for Disease Control and Prevention, Jul. 30, 2021, 9 pp., URL: https://www.cdc.gov/mmwr/volumes/70/wr/mm7031el.htm.
Hirano et al., "Early Outcome Prediction for Out-of-Hospital Cardiac Arrest with Initial Shockable Rhythm Using Machine Learning Models," Resuscitation, vol. 158, No. 145, Jan. 2021, pp. 49-56.
Hwang et al., "Assessing Accuracy of Wrist-Worn Wearable Devices in Measurement of Paroxysmal Supraventricular Tachycardia Heart Rate," Korean Circulation Journal, vol. 49, No. 5, May 2019, pp. 437-445.
Instructions for Irregular Rhythm Notification, Apple Inc., Jun. 2020, 154 pp.
International Search Report and Written Opinion of International Application No. PCT/US2022/016679, dated Jun. 9, 2022, 6 pp.
Koshy et al., "Smart Watches for Heart Rate Assessment in Atrial Arrhythmias," International Journal of Cardiology, vol. 266, Sep. 1, 2018, pp. 124-127.
Li et al., "The Current State of Mobile Phone Apps for Monitoring Heart Rate, Heart Rate Variability, and Atrial Fibrillation: Narrative Review," JMIR Mhealth Uhealth, vol. 7, No. 2, e11606, Feb. 15, 2019, 16 pp.
Medtronic Linq II, Medtronic CareLink Network, Jan. 29, 2021, 11 pp.
Mell et al., "Emergency Medical Services Response Times in Rural, Suburban, and Urban Areas," JAMA Surgery, vol. 152, No. 10, Oct. 2017, pp. 983-984.
Okubo et al., "Characteristics of Paediatric Out-of-Hospital Cardiac Arrest in the United States," Resuscitation, vol. 153, Apr. 27, 2020, pp. 227-233.
Papini et al., "Wearable Monitoring of Sleep-Disordered Breathing: Estimation of the Apnea-Hypopnea Index Using Wrist-Worn Reflective Photoplethysmography," Scientific Reports, vol. 10, No. 13512, Aug. 11, 2020, 15 pp.
Perez et al., "Large-Scale Assessment of a Smartwatch to Identify Atrial Fibrillation," The New England Journal of Medicine, vol. 381, No. 20, Nov. 14, 2019, pp. 1909-1917.
Pulsepoint, "Activate Citizen Response.", Building informed communities, 14 pp., Retrieved from the Internet on Oct. 25, 2021 from URL: ttps://www.pulsepoint.org.
Ringwald et al., "Smart Watch Recording of Ventricular Tachycardia: Case Study," American Journal of Emergency Medicine, vol. 38, No. 4, Apr. 1, 2020, pp. 849.e3-849.e5.
Roberts et al., "Best Buy makes deal to provide its senior services on Apple Watch", Star Tribune, Mar. 3, 2021, 2 pp., URL: https://www.startribune.com/best-buy-makes-deal-to-provide-its-senior-services-on-apple-watch/600029754/.
Rudner et al., "Interrogation of Patient Smartphone Activity Tracker to Assist Arrhythmia Management," Annals of Emergency Medicine, vol. 68, No. 3, Sep. 2016, pp. 292-294.
Salcido et al., "Have Outcomes After Out of Hospital Cardiac Arrest Improved Over Time?," Circulation: Cardiovascular Quality and Outcomes, vol. 14, No. 3, e007752, Mar. 2021, pp. 290-291.
Samani et al., "Robotic Automated External Defibrillator Ambulance for Emergency Medical Service in Smart Cities", vol. 4, IEEE, Jan. 4, 2016, pp. 268-283.
Samsung Galaxy Watch3 LTE Smartwatch, retrieved from https://www.samsung.com/us/watches/galaxywatch3/# health, on Apr. 29, 2021, 31 pp.
Seifert, "Say hello to Astro, Alexa on wheels", The Verge, Sep. 28, 2021, 18 pp., URL: https://www.theverge.com/2021/9/28/22697244/amazon-astro-home-robot-hands-on-features-price.
Seshadri et al., "Accuracy of Apple Watch for Detection of Atrial Fibrillation," Circulation, vol. 141, No. 8, Feb. 25, 2020, pp. 702-703.
Shcherbina et al., "Accuracy in Wrist-Worn, Sensor-Based Measurements of Heart Rate and Energy Expenditure in a Diverse Cohort," Journal of Personalized Medicine, vol. 3, No. 7, May 24, 2017, 12 pp.
Singh, "Detecting Atrial Fibrillation with with the Apple Watch: Our Clinically Validated Results," https://blog.cardiogr.am/detecting-atrial-fibrillation-with-the-apple-watch-our-clinically-validated-resultsea66163e0fa6, Mar. 21, 2018, 14 pp.
Singhal et al., "The Role of Wearables in Heart Failure," Current Heart Failure Reports, vol. 17, No. 4, Jun. 3, 2020, pp. 125-132.
Solomon et al., "Sudden Death in Patients with Myocardial Infarction and Left Ventricular Dysfunction, Heart Failure, or Both," vol. 352, No. 25, Jun. 23, 2005, pp. 2581-2588.
Sudden Cardiac Arrest Meeting the Challenge, The Joint Commission, 2011 (Applicant points out, in accordance with MPEP 609.04(a), that the year of publication, 2011, is sufficiently earlier than the effective U.S. filing date, so that the particular month of publication is not in issue.) 87 pp.
Tarakji et al., "Using a Novel Wireless System for Monitoring Patients After the Atrial Fibrillation Ablation Procedure: The iTransmit Study," Heart Rhythm Journal, vol. 12, No. 3, Mar. 1, 2015, pp. 554-559.
Than et al., "Machine Learning to Predict the Likelihood of Acute Myocardial Infarction," Circulation, vol. 140, Sep. 10, 2019, pp. 899-909.
Tuohy, "Amazon is now accepting your applications for its home surveillance drone", The Verge, Sep. 29, 2021, 9 pp., URL: https://www.theverge.com/2021/9/28/22692048/ring-always-home-cam-drone-amazon-price-release-date-specs.
Turakhia et al., "Rationale and Design of a Large-Scale, App-Based Study to Identify Cardiac Arrhythmias Using a Smartwatch: The Apple Heart Study," American Heart Journal, vol. 207, Jan. 2019, pp. 66-75.
U.S. Appl. No. 16/593,739, filed Oct. 4, 2019, by Haddad et al.
U.S. Appl. No. 17/006,444, filed Aug. 28, 2020, by Schulhauser.
U.S. Appl. No. 17/101,945, filed Nov. 23, 2020, by Anderson et al.
U.S. Appl. No. 17/301,923, filed Apr. 19, 2021, by Anderson et al.
U.S. Appl. No. 17/383,170, filed Jul. 22, 2021, naming inventors Haddad et al.
U.S. Appl. No. 17/459,713, filed Aug. 27, 2021, naming inventors Schulhauser et al.
U.S. Appl. No. 18/547,105, filed Feb. 16, 2022, naming inventors Stadler et al.
U.S. Appl. No. 18/549,227, filed Feb. 17, 2022, naming inventors Ousdigian et al.
U.S. Appl. No. 18/549,400, filed Feb. 10, 2022, naming inventors Krause et al.
U.S. Appl. No. 18/552,324, filed Feb. 17, 2022, naming inventors Sarkar et al.
U.S. Appl. No. 63/158,189, by Medtronic, Inc., filed Mar. 8, 2021.
U.S. Appl. No. 63/071,997, filed Aug. 28, 2020, naming inventors Schulhauser et al.
U.S. Appl. No. 63/158,189, filed Mar. 8, 2021, naming inventors Stadler et al.
U.S. Appl. No. 63/219,595, filed Jul. 8, 2021, naming inventors Gunderson et al.
U.S. Appl. No. 63/362,451, filed Apr. 4, 2022, naming inventors Galarneau et al.
Volosin et al., "Tachycardia detection performance of implantable loop recorders: results from a large 'real-life' patient cohort and patients with induced ventricular arrhythmias", Europace, vol. 15, No. 8, European Society of Cardiology, Aug. 1, 2013, pp. 1215-1222, URL: https://academic.oup.com/europace/article/15/8/1215/2398708.
Waldmann et al., "Temporal Trends of Out-of-Hospital Cardiac Arrests Without Resuscitation Attempt by Emergency Medical Services," Circulation: Cardiovascular Quality and Outcomes, vol. 14, No. e006626, Mar. 2021, pp. 279-289.
Wang et al., "Accuracy of Wrist-Worn Heart Rate Monitors," JAMA Cardiology, vol. 2, No. 1, Jan. 2017, pp. 104-106.

(56) References Cited

OTHER PUBLICATIONS

Wikipedia, "PulsePoint", Oct. 1, 2021, 12 pp., URL: https://en.wikipedia.org/wiki/PulsePoint.
Zaman et al., "Sudden Cardiac Death Early After Myocardial Infarction Pathogenesis, Risk Stratification, and Primary Prevention," Circulation, vol. 129, No. 23, Jun. 10, 2014, pp. 2426-2435.
U.S. Appl. No. 63/377,625, filed Sep. 29, 2022, naming inventors Grubac et al.
Brabant et al., "Effects of PEEP on the relationship between tidal volume and total impedance change measured via electrical impedance tomography (EIT)", Journal of Clinical Monitoring and Computing, vol. 36, Springer, Jan. 25, 2021, pp. 325-334.
De Vries et al., "Assessing breathing effort in mechanical ventilation: physiology and clinical implications", Annals of Translational Medicine, vol. 6, No. 19, May 30, 2018, 14 pp.
Huber, "Respiratory effort", BaluMed, Feb. 28, 2024, 3 pp., Retrieved from the Internet on Jan. 21, 2025 from URL: https://balumed.com/en/medical-dictionary/respiratory-effort.
U.S. Appl. No. 19/443,573, filed Jan. 8, 2026, naming inventors Stadler et al.
Communication pursuant to Article 94(3) EPC from counterpart European Application No. 22796313.9 dated Jun. 11, 2026, 5 pp.

* cited by examiner

RESPONSE BY ROBOTIC DEVICE TO AN ACUTE HEALTH EVENT REPORTED BY MEDICAL DEVICE

This application is a U.S. National Stage entry under 35 U.S.C. § 371 of International Application No. PCT/US2022/016679, filed Feb. 17, 2022, which claims priority from and the benefit of U.S. Provisional Patent Application Ser. No. 63/182,482, filed Apr. 30, 2021, the entire content of each of which is incorporated herein by reference.

FIELD

This disclosure generally relates to systems including medical devices and, more particularly, to monitoring of patient health using such systems.

BACKGROUND

A variety of devices are configured to configured to monitor physiological signals of a patient. Such devices include implantable or wearable medical devices, as well as a variety of wearable health or fitness tracking devices. The physiological signals sensed by such devices include as examples, electrocardiogram (ECG) signals, respiration signals, perfusion signals, activity and/or posture signals, pressure signals, blood oxygen saturation signals, body composition, and blood glucose or other blood constituent signals. In general, using these signals, such devices facilitate monitoring and evaluating patient health over a number of months or years, outside of a clinic setting.

In some cases, such devices are configured to detect acute health events based on the physiological signals, such as episodes of cardiac arrhythmia, myocardial infarction, stroke, or seizure. Example arrhythmia types include cardiac arrest (e.g., asystole), ventricular tachycardia (VT), and ventricular fibrillation (VF). The devices may store ECG and other physiological signal data collected during a time period including an episode as episode data. Such acute health events are associated with significant rates of death, particularly if not treated quickly.

For example, VF and other malignant tachyarrhythmias are the most commonly identified arrhythmia in sudden cardiac arrest (SCA) patients. If this arrhythmia continues for more than a few seconds, it may result in cardiogenic shock and cessation of effective blood circulation. The survival rate from SCA decreases between 7 and 10 percent for every minute that the patient waits for defibrillation. Consequently, sudden cardiac death (SCD) may result in a matter of minutes.

SUMMARY

In general, the disclosure describes techniques for confirming that a patient has experienced or is experiencing an acute health event that was reported by a medical device. In some examples, a robotic device receives a wirelessly transmitted message indicating detection of the acute health event from the medical device, e.g., an implantable medical device or a wearable device. Additionally or alternatively, a remote server may receive the message from the medical device and activate the robotic device. Processing circuitry, e.g., of the robotic device, may perform a variety of actions in response to the message, such as analyzing physiological data of the patient to confirm the acute health event, moving the robotic device to a location proximate to the patient to gather additional data, generating an alert, administering medication to the patient, and/or providing other medical treatment to the patient. The techniques described herein may reduce the time-to-treatment of the acute health event, reduce false alarms for acute health events, and/or reduce the workload of emergency medical personnel.

In one example, a method comprises determining, by processing circuitry of the robotic device, that a patient is experiencing or has experienced an acute health event; moving the robotic device to a location proximate the patient in response to determining that the patient is experiencing or has experienced the acute health event; gathering, by a sensor of the robotic device, physiological data from the patient after moving the robotic device to the location proximate the patient; confirming, by the processing circuitry, that the patient is experiencing or has experienced the acute health event based on the additional physiological data; and generating an output in response to confirming that the patient is experiencing or has experienced the acute health event.

In another example, a system comprises processing circuitry configured to perform any of the methods described herein.

In another example, a non-transitory computer readable storage medium comprises program instructions configured to cause processing circuitry to perform any of the methods described herein.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

Like reference characters refer to like elements throughout the figures and description.

DETAILED DESCRIPTION

Figure 1:
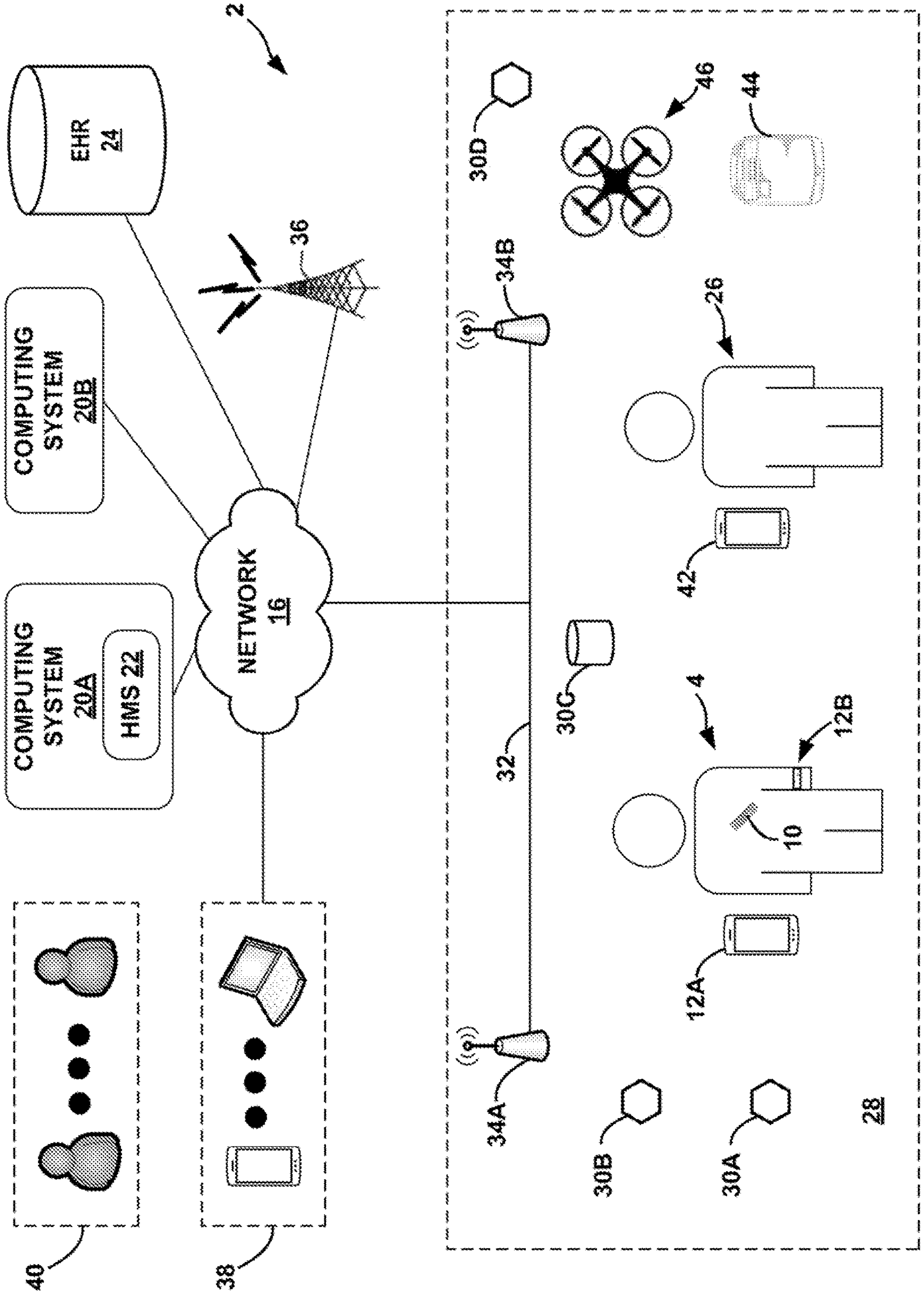
FIG. 1 is a block diagram illustrating an example system configured to detect acute health events of a patient, and to respond to such detections, in accordance with one or more techniques of this disclosure.

A variety of types of implantable and external devices are configured to detect arrhythmia episodes and other acute health events based on sensed ECGs and, in some cases, other physiological signals. External devices that may be used to non-invasively sense and monitor ECGs and other physiological signals include wearable devices with electrodes configured to contact the skin of the patient, such as patches, watches, or necklaces. Such external devices may facilitate relatively longer-term monitoring of patient health during normal daily activities.

Implantable medical devices (IMDs) also sense and monitor ECGs and other physiological signals, and detect acute health events such as episodes of arrhythmia, cardiac arrest, myocardial infarction, stroke, and seizure. Example IMDs include pacemakers and implantable cardioverter-defibrillators, which may be coupled to intravascular or extravascular leads, as well as pacemakers with housings configured for implantation within the heart, which may be leadless. Some IMDs do not provide therapy, such as implantable patient monitors. One example of such an IMD is the Reveal LINQ™ Insertable Cardiac Monitor (ICM) or the LINQ II™, available from Medtronic plc, which may be inserted subcutaneously. Such IMDs may facilitate relatively longer-term monitoring of patients during normal daily activities, and may periodically transmit collected data, e.g., episode data for detected arrhythmia episodes, to a remote patient monitoring system, such as the Medtronic Carelink™ Network.

This disclosure describes a robotic device configured to confirm whether a patient is experiencing or has experienced an acute health event. The robotic device may receive physiological data and/or an instruction message from a medical device, or from a device (e.g., remote server) communicatively coupled to the medical device, that indicates an acute health event or supports the determination that the patient has experienced an acute health event. The robotic device can move close enough to the patient to sense additional physiological data to confirm the acute health event. In response to confirming that the acute health event has occurred or is occurring, the robotic device may be configured to generate an output by, for example, administering medical treatment and/or contacting another person to come to the aid of the patient.

Most acute health events go unwitnessed, and the most critical need is immediate application of CPR. During an unwitnessed event, the person in distress may be alone and unable to communicate with others. Depending on the circumstances of the acute health event, there may be a need to find nearby bystanders and alert them that the patient needs CPR and perhaps other medical tasks. The robotic device may be configured to administer CPR and/or support the administration of CPR by a another person. An autonomous robotic device may be configured to identify and alert the closest human that help is needed. In response to determining that there are no witnesses to an acute health event experienced by a patient, the robotic device may be configured to take action to confirm the event and/or administer medical treatment, either directly or by instructing a bystander.

FIG. 1 is a block diagram illustrating an example system 2 configured to detect acute health events of a patient 4, and to respond to such detection, in accordance with one or more techniques of this disclosure. As used herein, the terms "detect," "detection," and the like may refer to detection of an acute health event presently (at the time the data is collected) being experienced by patient 4, as well as detection based on the data that the condition of patient 4 is such that they have a suprathreshold likelihood of experiencing the event within a particular timeframe, e.g., prediction of the acute health event. The example techniques may be used with one or more patient sensing devices, e.g., IMD 10, which may be in wireless communication with one or more patient computing devices, e.g., patient computing devices 12A and 12B (collectively, "patient computing devices 12") and/or robotic device 46. Although not illustrated in FIG. 1, IMD 10 include electrodes and other sensors to sense physiological signals of patient 4, and may collect and store sensed physiological data based on the signals and detect episodes based on the data.

IMD 10 may be implanted outside of a thoracic cavity of patient 4 (e.g., subcutaneously in the pectoral location illustrated in FIG. 1). IMD 10 may be positioned near the sternum near or just below the level of the heart of patient 4, e.g., at least partially within the cardiac silhouette. In some examples, IMD 10 takes the form of the LINQ™ ICM or the LINQ II™. Although described primarily in the context of examples in which IMD 10 takes the form of an ICM, the techniques of this disclosure may be implemented in systems including any one or more implantable or external medical devices, including monitors, pacemakers, defibrillators, wearable external defibrillators, neurostimulators, or drug pumps. Furthermore, although described primarily in the context of examples including a single implanted patient sensing device, in some examples a system includes one or more patient sensing devices, which may be implanted within patient 4 or external to (e.g., worn by) patient 4.

Patient computing devices 12 are configured for wireless communication with IMD 10 and/or robotic device 46. Computing devices 12 retrieve event data and other sensed physiological data from IMD 10 that was collected and stored by the IMD. In some examples, computing devices 12 take the form of personal computing devices of patient 4. For example, computing device 12A may take the form of a smartphone of patient 4, and computing device 12B may take the form of a smartwatch or other smart apparel of patient 4. In some examples, computing devices 12 may be any computing device configured for wireless communication with IMD 10, such as a desktop, laptop, or tablet computer. Computing devices 12 may communicate with IMD 10 and each other according to the Bluetooth® or Bluetooth® Low Energy (BLE) protocols, as examples. In some examples, only one of computing devices 12, e.g., computing device 12A, is configured for communication with IMD 10, e.g., due to execution of software (e.g., part of a health monitoring application as described herein) enabling communication and interaction with an IMD.

In some examples, computing device(s) 12, e.g., wearable computing device 12B in the example illustrated by FIG. 1A, may include electrodes and other sensors to sense physiological signals of patient 4, and may collect and store physiological data and detect episodes based on such signals. Computing device 12B may be incorporated into the apparel of patient 14, such as within clothing, shoes, eyeglasses, a watch, a ring, a bracelet or wristband, a necklace, an anklet, a belt, a hat, etc. In some examples, computing device 12B is a smartwatch or other accessory or peripheral for a smartphone computing device 12A.

One or more of computing devices 12 may be configured to communicate with a variety of other devices or systems via a network 16. For example, one or more of computing devices 12 may be configured to communicate with one or more computing systems, e.g., computing systems 20A and 20B (collectively, "computing systems 20") via network 16, where one of computing systems 20A and 20B may be part of a robotic device. Computing systems 20A and 20B may be respectively managed by manufacturers of IMD 10 and computing devices 12 to, for example, provide cloud storage and analysis of collected data, maintenance and software services, or other networked functionality for their respective devices and users thereof. Computing system 20A may comprise, or may be implemented by, the Medtronic Carelink™ Network, in some examples. In the example illustrated by FIG. 1, computing system 20A implements a health monitoring system (HMS) 22, although in other examples, either of both of computing systems 20 may implement HMS 22. As will be described in greater detail below, HMS 22 facilities detection of acute health events of patient 4 by system 2, and the responses of system 2 to such acute health events.

Although this disclosure describes specific functions being performed by devices 10, 12, 30, 38, and 46 and systems 20 and 22, any of these devices or systems may be configured to perform one or more of the techniques described herein. For example, any of devices 10, 12, 30, 38, and 46 and systems 20 and 22 may be configured to determine that patient 4 is experiencing or has experienced an acute health event. Additionally or alternatively, any of devices 10, 12, 30, 38, and 46 and systems 20 and 22 may be configured to contact another person to come to the aid of patient 4. Moreover, any of devices 10, 12, 30, 38, and 46 and systems 20 and 22 may be configured to determine a medical treatment based on the acute health event to administer to patient 4.

Computing device(s) 12 may transmit data, including data retrieved from IMD 10, to computing system(s) 20 via network 16. The data may include sensed data, e.g., values of physiological parameters measured by IMD 10 and, in some cases one or more of computing devices 12, data regarding episodes of arrhythmia or other acute health events detected by IMD 10 and computing device(s) 12, and other physiological signals or data recorded by IMD 10 and/or computing device(s) 12. HMS 22 may also retrieve data regarding patient 4 from one or more sources of electronic health records (EHR) 24 via network. EHR 24 may include data regarding historical (e.g., baseline) physiological parameter values, previous health events and treatments, disease states, comorbidities, demographics, height, weight, and body mass index (BMI), as examples, of patients including patient 4. HMS 22 may use data from EHR 24 to configure algorithms implemented by IMD 10 and/or computing devices 12 to detect acute health events for patient 4. In some examples, HMS 22 provides data from EHR 24 to computing device(s) 12 and/or IMD 10 for storage therein and use as part of their algorithms for detecting acute health events.

IMD 10 and/or computing devices 12 may be configured to directly or indirectly communicate with robotic device 46 that is configured to confirm whether an acute health event has occurred or is occurring. For example, IMD 10 and/or computing devices 12 may be communicatively coupled with robotic device 46 via a Bluetooth connection. IMD 10 and/or computing devices 12 may be communicatively coupled with robotic device 46 through an intermediate computing device (e.g., computing device 12A or IoT device 30) that is communicatively coupled with robotic device 46. IMD 10 and/or computing devices 12 may be communicatively coupled with robotic device 46 through HMS 22, through Wi-Fi access points 34, or through a cellular network via base station 36. In some examples, robotic device 46 is at a remote location, and IMD 10 and/or computing devices 12 contact HMS 22 via cellular communication or other means to request that robotic device 46 travel to the patient 4.

IMD 10 and/or computing device 12B may be configured to sense and transmit physiological data to the robotic device. In some examples, IMD 10 and/or computing device 12B are configured to analyze the physiological data and determine whether the physiological data indicates that patient 4 has experienced or is experiencing an acute health event. IMD 10 and/or computing device 12B can send an indication of the acute health event to the robotic device. In some examples, the phrase "medical device attached to patient 4" may include implanted devices and wearable devices such as IMD 10, computing device 12A, and/or computing device 12B.

Network 16 may include one or more computing devices, such as one or more non-edge switches, routers, hubs, gateways, security devices such as firewalls, intrusion detection, and/or intrusion prevention devices, servers, cellular base stations and nodes, wireless access points, bridges, cable modems, application accelerators, or other network devices. Network 16 may include one or more networks administered by service providers, and may thus form part of a large-scale public network infrastructure, e.g., the Internet. Network 16 may provide computing devices and systems, such as those illustrated in FIG. 1, access to the Internet, and may provide a communication framework that allows the computing devices and systems to communicate with one another. In some examples, network 16 may include a private network that provides a communication framework that allows the computing devices and systems illustrated in FIG. 1 to communicate with each other, but isolates some of the data flows from devices external to the private network for security purposes. In some examples, the communications between the computing devices and systems illustrated in FIG. 1 are encrypted.

As will be described herein, IMD 10 may be configured to detect acute health events of patient 4 based on data sensed by IMD 10 and, in some cases, other data, such as data sensed by computing devices 12A and/or 12B, and data from EHR 24. In response to detection of an acute health event, IMD 10 may wirelessly transmit a message to one or both of computing devices 12A and 12B. The message may indicate that IMD 10 detected an acute health event of the patient. The message may indicate a time that IMD 10 detected the acute health event. The message may include physiological data collected by IMD 10, e.g., data which lead to detection of the acute health event, data prior to detection of the acute health event, and/or real-time or more recent data collected after detection of the acute health event. The physiological data may include values of one or more physiological parameters and/or digitized physiological signals. Examples of acute health events are a cardiac arrest, a ventricular fibrillation, a ventricular tachycardia, myocardial infarction, a pause in heart rhythm (asystole), or Pulseless Electrical Activity (PEA), acute respiratory distress syndrome (ARDS, a stroke, a seizure, or a fall.

In response to the message from IMD 10, computing device(s) 12 may output an alarm that may be visual and/or audible, and configured to immediately attract the attention of patient 4 or any person in environment 28 with patient 4, e.g., a bystander 26. Environment 28 may be a home, office, or place of business, or public venue, as examples. Computing device(s) 12 may also transmit a message to HMS 22 via network 16. The message may include the data received from IMD 10 and, in some cases, additional data collected by computing device(s) 12 or other devices in response to the detection of the acute health event by IMD 10. For example, the message may include a location of patient 4 determined by computing device(s) 12.

Other devices in the environment 28 of patient 4 may also be configured to output alarms or take other actions to attract the attention of patient 4 and, possibly, a bystander 26, or to otherwise facilitate the delivery of care to patient 4. For example, environment 28 may include one or more Internet of Things (IoT) devices, such as IoT devices 30A-30D (collectively "IoT devices 30") illustrated in the example of FIG. 1. IoT devices 30 may include, as examples, so called "smart" speakers, cameras, lights, locks, thermostats, appliances, actuators, controllers, or any other smart home (or building) devices. In the example of FIG. 1, IoT device 30C is a smart speaker and/or controller, which may include a display. IoT devices 30 may provide audible and/or visual alarms when configured with output devices to do so. As other examples, IoT devices 30 may cause smart lights throughout environment 28 to flash or blink and unlock doors. In some examples, IoT devices 30 that include cameras or other sensors may activate those sensors to collect data regarding patient 4, e.g., for evaluation of the condition of patient 4.

IoT devices 30, such as one or more smart speakers, may be configured to detect acute health events by monitoring sound to detect agonal breathing or other physiological indicators. IoT devices 30 may be configured to also detect acute health events by sensing physiological data captured from optical sensors or sonar sensors. Non-wearable and non-implanted devices such as IoT devices 30 may be configured to perform techniques ascribed to IMD 10, computing devices 12, and computing systems 20 such as sensing physiological signals, determining that acute health events have occurred, transmitting physiological data to other devices, and/or generating alerts.

Computing device(s) 12 may be configured to wirelessly communicate with IoT devices 30 to cause IoT devices 30 to take the actions described herein. In some examples, HMS 22 communicates with IoT devices 30 via network 16 to cause IoT devices 30 to take the actions described herein, e.g., in response to receiving the alert message from computing device(s) 12 as described above. In some examples, IMD 10 is configured to communicate wirelessly with one or more of IoT devices 30, e.g., in response to detection of an acute health event when communication with computing devices 12 is unavailable. In such examples, IoT device(s) 30 may be configured to provide some or all of the functionality ascribed to computing devices 12 herein.

Environment 28 includes computing facilities, e.g., a local network 32, by which computing devices 12, IoT devices 30, and other devices within environment 28 may communicate via network 16, e.g., with HMS 22. For example, environment 28 may be configured with wireless technology, such as IEEE 802.11 wireless networks, IEEE 802.15 ZigBee networks, an ultra-wideband protocol, near-field communication, or the like. Environment 28 may include one or more wireless access points, e.g., wireless access points 34A and 34B (collectively, "wireless access points 34") that provide support for wireless communications throughout environment 28. Additionally or alternatively, e.g., when local network is unavailable, computing devices 12, IoT devices 30, and other devices within environment 28 may be configured to communicate with network 16, e.g., with HMS 22, via a cellular base station 36 and a cellular network.

Computing device(s) 12, and in some examples IoT devices 30, may include input devices and interfaces to allow a user to override the alarm in the event the detection of the acute health event by IMD 10 was false. In some examples, one or more of computing device(s) 12 and IoT device(s) 30 may implement an event assistant. The event assistant may provide a conversational interface for patient 4 and/or bystander 26 to exchange information with the computing device or IoT device. The event assistant may query the user regarding the condition of patient 4 in response to receiving the alert message from IMD 10. Responses from the user may be used to confirm or override detection of the acute health event by IMD 10, or to provide additional information about the acute health event or the condition of patient 4 more generally that may improve the efficacy of the treatment of patient 4. For example, information received by the event assistant may be used to provide an indication of severity or type (differential diagnosis) for the acute health event. The event assistant may use natural language processing and context data to interpret utterances by the user. In some examples, in addition to receiving responses to queries posed by the assistant, the event assistant may be configured to respond to queries posed by the user. For example, patient 4 may indicate that they feel dizzy and ask the event assistant, "how am I doing?".

In some examples, computing device(s) 12 and/or HMS 22 may implement one or more algorithms to evaluate the sensed physiological data received from IMD 10, and in some cases additional physiological or other data sensed or otherwise collected by the computing device(s) or IoT devices 30, to confirm or override the detection of the acute health event by IMD 10. In some examples, computing device(s) 12 and/or computing system(s) 20 may have greater processing capacity than IMD 10, enabling more complex analysis of the data. In some examples, the computing device(s) 12 and/or HMS 22 may apply the data to a machine learning model or other artificial intelligence developed algorithm, e.g., to determine whether the data is sufficiently indicative of the acute health event.

In examples in which computing device(s) 12 are configured to perform an acute health event confirmation analysis, computing device(s) 12 may transmit alert messages to HMS 22, emergency medical services, and/or IoT devices 30 in response to confirming the acute health event. In some examples, computing device(s) 12 may be configured to transmit the alert messages prior to completing the confirmation analysis, and transmit cancellation messages in response to the analysis overriding the detection of the acute health event by IMD 10. HMS 22 may be configured to perform a number of operations in response to receiving an alert message from computing device(s) 12 and/or IoT device(s) 30. HMS 22 may be configured to cancel such operations in response to receiving a cancellation message from computing device(s) 12 and/or IoT device(s) 30.

For example, HMS 22 may be configured to transmit alert messages to one or computing devices 38 associated with one or more care providers 40 via network 16. Care providers may include emergency medical systems (EMS) and hospitals, and may include particular departments within a hospital, such as an emergency department, catheterization lab, or a stroke response department. Computing devices 38 may include smartphones, desktop, laptop, or tablet computers, or workstations associated with such systems or entities, or employees of such systems or entities. The alert messages may include any of the data collected by IMD 10, computing device(s) 12, and IoT device(s) 30, including sensed physiological data, time of the acute health event, location of patient 4, and results of the analysis by IMD 10, computing device(s) 12, IoT device(s) 30, and/or HMS 22.

The information transmitted from HMS 22 to care providers 40 may improve the timeliness and effectiveness of treatment of the acute health event of patient 4 by care providers 40. In some examples, instead of or in addition to HMS 22 providing an alert message to one or more computing devices 38 associated with an EMS care provider 40, computing device(s) 12 and/or IoT devices 30 may be configured to automatically contact EMS, e.g., use the telephone system to contact a 911 call center, autodial 911, in response to receiving an alert message from IMD 10. Again, such operations may be cancelled by patient 4, bystander 26, or another user via a user interface of computing device(s) 12 or IoT device(s) 30, or automatically cancelled by computing device(s) 12 based on a confirmatory analysis performed by the computing device(s) overriding the detection of the acute health event by IMD 10.

Similarly, HMS 22 may be configured to transmit an alert message to computing device 42 of bystander 26, which may improve the timeliness and effectiveness of treatment of the acute health event of patient 4 by bystander 26. Computing device 42 may be similar to computing devices 12 and computing devices 38, e.g., a smartphone. In some examples, HMS 22 may determine that bystander 26 is proximate to patient 4 based on a location of patient 4 (e.g., a first location), e.g., received from computing device(s) 12, and a location of computing device 42 (e.g., a second location), e.g., reported to HMS 22 by an application implemented on computing device 42. In some examples, HMS 22 may transmit the alert message to any computing devices 42 in an alert area determined based on the location of patient 4, e.g., by transmitting the alert message to all computing devices in communication with base station 36.

In some examples, the alert message to bystander 26 may be configured to assist a layperson in treating patient. For example, the alert message to bystander 26 may include a location (and in some cases a description) of patient 4, the general nature of the acute health event, directions for providing care to patient 4, such as directions for providing cardio-pulmonary resuscitation (CPR), a location of nearby medical equipment for treatment of patient 4, such as a life vest or an automated external defibrillator (AED) 44, and instructions for use of the equipment. In some examples, computing device(s) 12, IoT device(s) 30, and/or computing device 42 may implement an event assistant configured to use natural language processing and context data to provide a conversational interface for bystander 42. The assistant may provide bystander 26 with directions for providing care to patient 4, and respond to queries from bystander 26 about how to provide care to patient 4.

In some examples, HMS 22 may mediate bi-directional audio (and in some cases video) communication between care providers 40 and patient 4 or bystander 26. Such communication may allow care providers 40 to evaluate the condition of patient 4, e.g., through communication with patient 4 or bystander 26, or through use of a camera or other sensors of the computing device or IoT device, in advance of the time they will begin caring for the patient, which may improve the efficacy of care delivered to the patient. Such communication may also allow the care providers to instruct bystander 42 regarding first responder treatment of patient 4.

In some examples, HMS 22 or devices 10, 12, 30, or 38 may control dispatch of a robotic device 46 to environment 28, or a location near environment 28 or patient 4. For example, a care management service or a remote patient monitoring system (e.g., the Medtronic Carelink™ Network) may be configured to contact and instruct robotic device 46 to take action. Robotic device 46 may be a robot, a drone-like device, a ground-based device, a marine-based device, and/or unmanned aerial vehicle (UAV). Robotic device 46 may include means for flying, rolling, hovering, climbing stairs, opening doors, and/or maneuvering around, over, or through obstacles. Robotic device 46 may be equipped with a number of sensors and/or actuators to perform a number of operations. For example, robotic device 46 may include a camera or other sensors to navigate to its intended location, identify patient 4 and, in some cases, bystander 26, and to evaluate a condition of patient.

Robotic device 46 may be configured to sense physiological signals (e.g., an ECG, pulse, or other measurement) or to act as an AED by touching two parts of the patient body with extendable arms, where each arm may include an electrode. In some examples, robotic device 46 may include one or more movable arms with optical sensor(s), microphone(s), thermal sensor(s), and/or any other sensors for receiving physiological signals. In some examples, robotic device 46 may include user interface devices to communicate with patient 4 and/or bystander 26. In some examples, robotic device 46 may provide directions to bystander 26, to the location of patient 4 and regarding how to provide first responder care, such as CPR, to patient 4. In some examples, robotic device 46 may carry medical equipment, e.g., AED 44, and/or medication to the location of patient 4.

Figure 2:
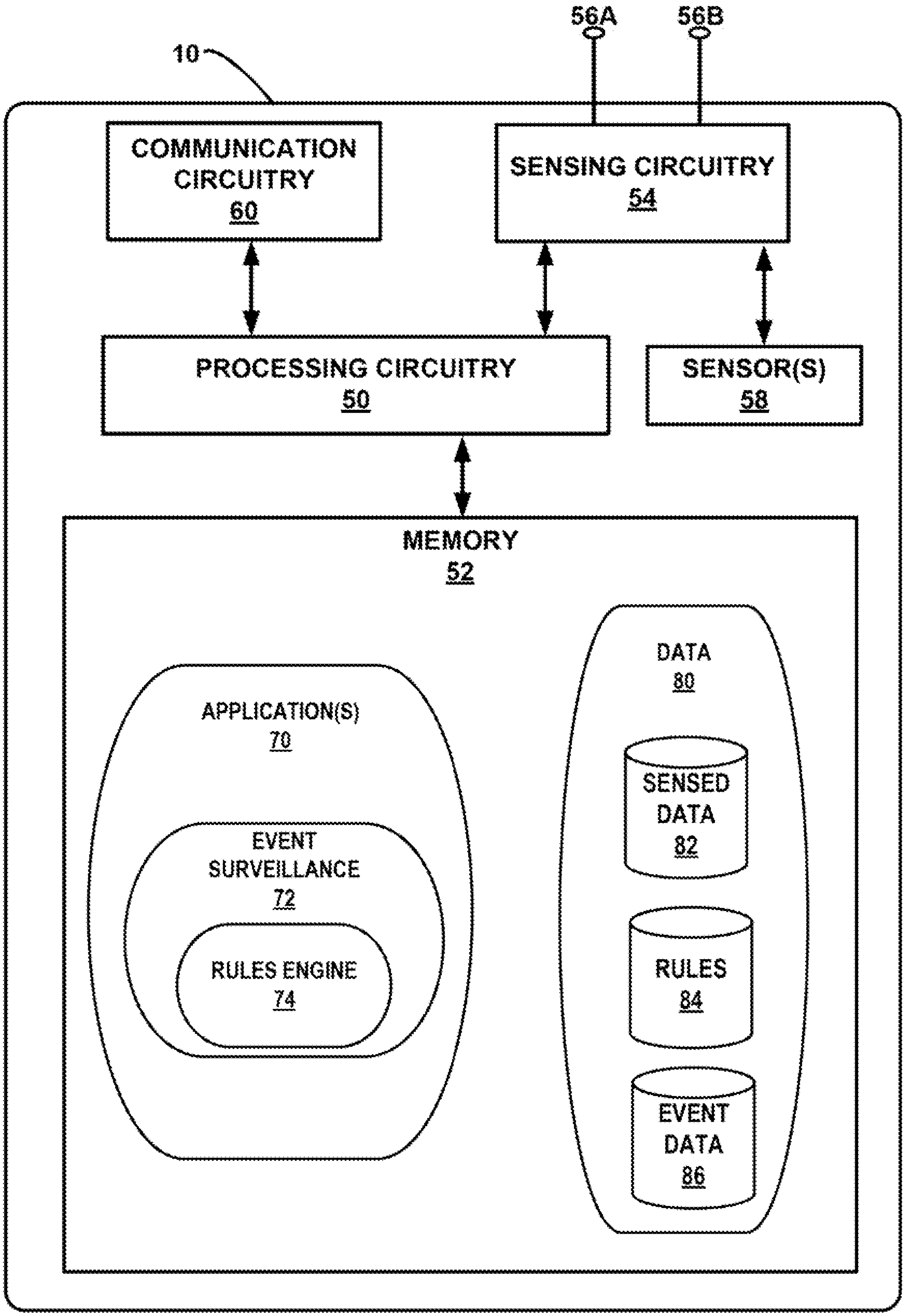
FIG. 2 is a block diagram illustrating an example configuration of a patient sensing device that operates in accordance with one or more techniques of the present disclosure.

FIG. 2 is a block diagram illustrating an example configuration of IMD 10 of FIG. 1. As shown in FIG. 2, IMD 10 includes processing circuitry 50, memory 52, sensing circuitry 54 coupled to electrodes 56A and 56B (hereinafter, "electrodes 56") and one or more sensor(s) 58, and communication circuitry 60.

Processing circuitry 50 may include fixed function circuitry and/or programmable processing circuitry. Processing circuitry 50 may include any one or more of a microprocessor, a controller, a graphics processing unit (GPU), a tensor processing unit (TPU), a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more GPUs, one or more TPUs, one or more DSPs, one or more ASICs, or one or more FPGAs, as well as other discrete or integrated logic circuitry. The functions attributed to processing circuitry 50 herein may be embodied as software, firmware, hardware, or any combination thereof. In some examples, memory 53 includes computer-readable instructions that, when executed by processing circuitry 50, cause IMD 10 and processing circuitry 50 to perform various functions attributed herein to IMD 10 and processing circuitry 50. Memory 53 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Sensing circuitry 54 may monitor signals from electrodes 56 in order to, for example, monitor electrical activity of a heart of patient 4 and produce ECG data for patient 4. In some examples, processing circuitry 50 may identify features of the sensed ECG, such as heart rate, heart rate variability, intra-beat intervals, and/or ECG morphologic features, to detect an episode of cardiac arrhythmia of patient 4. Processing circuitry 50 may store the digitized ECG and features of the ECG used to detect the arrhythmia episode in memory 52 as episode data for the detected arrhythmia episode.

In some examples, sensing circuitry 54 measures impedance, e.g., of tissue proximate to IMD 10, via electrodes 56. The measured impedance may vary based on respiration and a degree of perfusion or edema. Processing circuitry 50 may determine physiological data relating to respiration, perfusion, and/or edema based on the measured impedance.

In some examples, IMD 10 includes one or more sensors 58, such as one or more accelerometers, microphones, optical sensors, temperature sensors, and/or pressure sensors. In some examples, sensing circuitry 54 may include one or more filters and amplifiers for filtering and amplifying signals received from one or more of electrodes 56 and/or sensors 58. In some examples, sensing circuitry 54 and/or processing circuitry 50 may include a rectifier, filter and/or amplifier, a sense amplifier, comparator, and/or analog-to-digital converter. Processing circuitry 50 may determine physiological data, e.g., values of physiological parameters of patient 4, based on signals from sensors 58, which may be stored in memory 52.

Memory 52 may store applications 70 executable by processing circuitry 50, and data 80. Applications 70 may include an acute health event surveillance application 72. Processing circuitry 50 may execute event surveillance application 72 to detect an acute health event of patient 4 based on combination of one or more of the types of physiological data described herein, which may be stored as sensed data 82. In some examples, sensed data 82 may additionally include data sensed by other devices, e.g., computing device(s) 12, and received via communication circuitry 60. Event surveillance application 72 may be configured with a rules engine 74. Rules engine 74 may apply rules 84 to sensed data 82. Rules 84 may include one or more models, algorithms, decision trees, and/or thresholds. In some cases, rules 84 may be developed based on machine learning.

As examples, event surveillance application 72 may detect a cardiac arrest, a ventricular fibrillation, a ventricular tachycardia, a cardiac pause of asystole, pulseless electrical activity (PEA), or a myocardial infarction based on an ECG and/or other physiological data indicating the electrical or mechanical activity of heart 6 of patient 4 (FIG. 1). In some examples, event surveillance application 72 may detect stroke based on such cardiac activity data. In some examples, sensing circuitry 54 may detect brain activity data, e.g., an electroencephalogram (EEG) via electrodes 56, and event surveillance application 72 may detect stroke or a seizure based on the brain activity alone, or in combination with cardiac activity data or other physiological data. In some examples, event surveillance application 72 detects whether the patient has fallen based on data from an accelerometer alone, or in combination with other physiological data. When event surveillance application 72 detects an acute health event, event surveillance application 72 may store the sensed data 82 that lead to the detection (and in some cases a window of data preceding and/or following the detection) as event data 86.

In some examples, in response to detection of an acute health event, processing circuitry 50 transmits, via communication circuitry 60, event data 86 for the event to computing device(s) 12 (FIG. 1). This transmission may be included in a message indicating the acute health event, as described herein. Transmission of the message may occur on an ad hoc basis and as quickly as possible. Communication circuitry 60 may include any suitable hardware, firmware, software, or any combination thereof for wirelessly communicating with another device, such as computing devices 12, IoT devices 30, and/or robotic devices.

Figure 3:
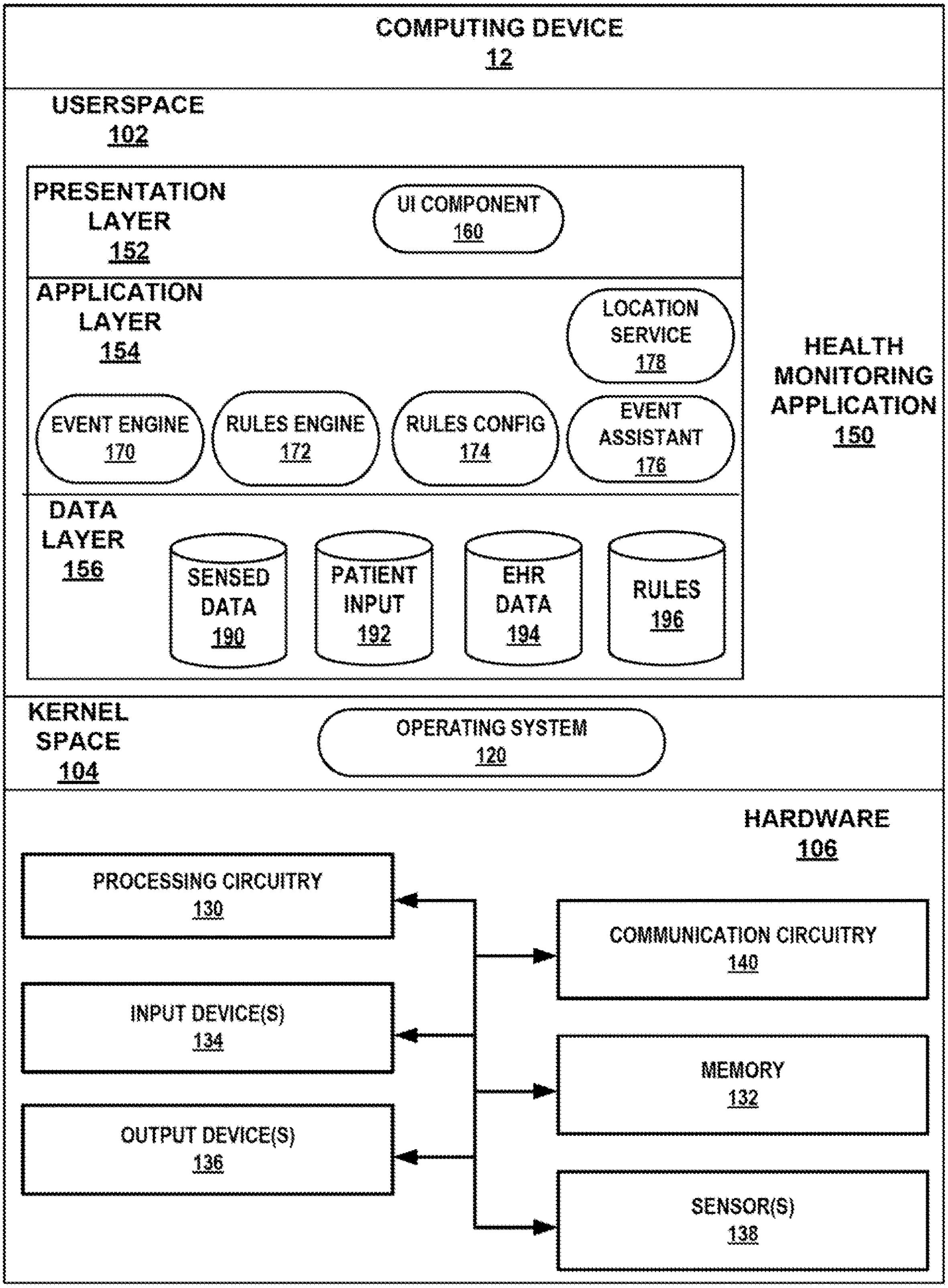
FIG. 3 is block diagram illustrating an example configuration of a computing device that operates in accordance with one or more techniques of the present disclosure.

FIG. 3 is a block diagram illustrating an example configuration of a computing device 12 of patient 4, which may correspond to either (or both operating in coordination) of computing devices 12A and 12B illustrated in FIG. 1. In some examples, computing device 12 takes the form of a smartphone, a laptop, a tablet computer, a personal digital assistant (PDA), a smartwatch or other wearable computing device. In some examples, IoT devices 30 may be configured similarly to the configuration of computing device 12 illustrated in FIG. 3.

As shown in the example of FIG. 3, computing device 12 may be logically divided into user space 102, kernel space 104, and hardware 106. Hardware 106 may include one or more hardware components that provide an operating environment for components executing in user space 102 and kernel space 104. User space 102 and kernel space 104 may represent different sections or segmentations of memory, where kernel space 104 provides higher privileges to processes and threads than user space 102. For instance, kernel space 104 may include operating system 120, which operates with higher privileges than components executing in user space 102.

As shown in FIG. 3, hardware 106 includes processing circuitry 130, memory 132, one or more input devices 134, one or more output devices 136, one or more sensors 138, and communication circuitry 140. Although shown in FIG. 3 as a stand-alone device for purposes of example, computing device 12 may be any component or system that includes processing circuitry or other suitable computing environment for executing software instructions and, for example, need not necessarily include one or more elements shown in FIG. 3.

Processing circuitry 130 is configured to implement functionality and/or process instructions for execution within computing device 12. For example, processing circuitry 130 may be configured to receive and process instructions stored in memory 132 that provide functionality of components included in kernel space 104 and user space 102 to perform one or more operations in accordance with techniques of this disclosure. Examples of processing circuitry 130 may include, any one or more microprocessors, controllers, GPUs, TPUs, DSPs, ASICs, FPGAs, or equivalent discrete or integrated logic circuitry.

Memory 132 may be configured to store information within computing device 12, for processing during operation of computing device 12. Memory 132, in some examples, is described as a computer-readable storage medium. In some examples, memory 132 includes a temporary memory or a volatile memory. Examples of volatile memories include random access memories (RAM), dynamic random access memories (DRAM), static random access memories (SRAM), and other forms of volatile memories known in the art. Memory 132, in some examples, also includes one or more memories configured for long-term storage of information, e.g. including non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

One or more input devices 134 of computing device 12 may receive input, e.g., from patient 4 or another user. Examples of input are tactile, audio, kinetic, and optical input. Input devices 134 may include, as examples, a mouse, keyboard, voice responsive system, camera, buttons, control pad, microphone, presence-sensitive or touch-sensitive component (e.g., screen), or any other device for detecting input from a user or a machine.

One or more output devices 136 of computing device 12 may generate output, e.g., to patient 4 or another user. Examples of output are tactile, audio, and visual output. Output devices 134 of computing device 12 may include a presence-sensitive screen, sound card, video graphics adapter card, speaker, cathode ray tube (CRT) monitor, liquid crystal display (LCD), light emitting diodes (LEDs), or any type of device for generating tactile, audio, and/or visual output.

One or more sensors 138 of computing device 12 may sense physiological parameters or signals of patient 4. Sensor(s) 138 may include electrodes, three-axis accelerometers, an optical sensor, impedance sensors, temperature sensors, pressure sensors, heart sounds sensors, and other sensors, and sensing circuitry (e.g., including an ADC), similar to those described above with respect to IMD 10 and FIG. 2.

Communication circuitry 140 of computing device 12 may communicate with other devices by transmitting and receiving data. Communication circuitry 140 may include a network interface card, such as an Ethernet card, an optical transceiver, a radio frequency transceiver, or any other type of device that can send and receive information. For example, communication circuitry 140 may include a radio transceiver configured for communication according to standards or protocols, such as 3G, 4G, 5G, Wi-Fi (e.g., IEEE 802.11 or IEEE 802.15 ZigBee), Bluetooth®, or Bluetooth® Low Energy (BLE). Communication circuitry 140 may be configured to communicate with a robotic device by, for example, sending physiological data to the robotic device and/or sending a location signal to the robotic device. The location signal may indicate the location of the patient (e.g., the first location) or the location of computing device 12 (e.g., the second location).

As shown in FIG. 3, health monitoring application 150 executes in user space 102 of computing device 12. Health monitoring application 150 may be logically divided into presentation layer 152, application layer 154, and data layer 156. Presentation layer 152 may include a user interface (UI) component 160, which generates and renders user interfaces of health monitoring application 150.

Application layer 154 may include, but is not limited to, an event engine 170, rules engine 172, rules configuration component 174, event assistant 176, and location service 178. Event engine 172 may be responsive to receipt of an alert transmission from IMD 10 indicating that IMD 10 detected an acute health event. Event engine 172 may control performance of any of the operations in response to detection of an acute health event ascribed herein to computing device 12, such as activating an alarm, transmitting alert messages to HMS 22, controlling IoT devices 30, and analyzing data to confirm or override the detection of the acute health event by IMD 10.

Rules engine 174 analyzes sensed data 190, and in some examples, patient input 192 and/or EHR data 194, to determine whether there is a sufficient likelihood that patient 4 is experiencing the acute health event detected by IMD 10. Sensed data 190 may include data received from IMD 10 as part of the alert transmission, additional data transmitted from IMD 10, e.g., in "real-time," and physiological and other data related to the condition of patient 4 collected by computing device(s) 12 and/or IoT devices 30. As examples sensed data 190 from computing device(s) 12 may include one or more of: activity levels, walking/running distance, resting energy, active energy, exercise minutes, quantifications of standing, body mass, body mass index, heart rate, low, high, and/or irregular heart rate events, heart rate variability, walking heart rate, heart beat series, digitized ECG, blood oxygen saturation, blood pressure (systolic and/or diastolic), respiratory rate, maximum volume of oxygen, blood glucose, peripheral perfusion, and sleep patterns.

Patient input 192 may include responses to queries posed by health monitoring application 150 regarding the condition of patient 4, input by patient 4 or another user, such as bystander 26. The queries and responses may occur responsive to the detection of the event by IMD 10, or may have occurred prior to the detection, e.g., as part long-term monitoring of the health of patient 4. User recorded health data may include one or more of: exercise and activity data, sleep data, symptom data, medical history data, quality of life data, nutrition data, medication taking or compliance data, allergy data, demographic data, weight, and height. EHR data 194 may include any of the information regarding the historical condition or treatments of patient 4 described above. EHR data 194 may relate to history of cardiac arrest, tachyarrhythmia, myocardial infarction, stroke, seizure, chronic obstructive pulmonary disease (COPD), renal dysfunction, or hypertension, history of procedures, such as ablation or cardioversion, and healthcare utilization. EHR data 194 may also include demographic and other information of patient 4, such as age, gender, height, weight, and BMI.

Rules engine 172 may apply rules 196 to the data. Rules 196 may include one or more models, algorithms, decision trees, and/or thresholds. In some cases, rules 196 may be developed based on machine learning. In some examples, rules 196 and the operation of rules engine 172 may provide a more complex analysis the data, even the sensed data received from IMD 10, than is provided by rules engine 74 and rules 84. In some examples, rules 196 include one or more models developed by machine learning, and rules engine 172 applies feature vectors derived from the data to the model(s).

Rules configuration component 174 may be configured to modify rules 196 (and in some examples rules 84) based on feedback indicating whether the detections and confirmations of acute health events by IMD 10 and computing device 12 were accurate. The feedback may be received from patient 4, or from care providers 40 and/or EHR 24 via HMS 22. In some examples, rules configuration component 174 may utilize the data sets from true and false detections and confirmations for supervised machine learning to further train models included as part of rules 196.

As discussed above, event assistant 176 may provide a conversational interface for patient 4 and/or bystander 26 to exchange information with computing device 12. Event assistant 176 may query the user regarding the condition of patient 4 in response to receiving the alert message from IMD 10. Responses from the user may be included as patient input 192. Event assistant 176 may use natural language processing and context data to interpret utterances by the user. In some examples, in addition to receiving responses to queries posed by the assistant, event assistant 176 may be configured to respond to queries posed by the user. In some examples, event assistant 176 may provide directions to and respond to queries regarding treatment of patient 4 from patient 4 or bystander 26.

Location service 178 may determine the location of computing device 12 and, thereby, the presumed location of patient 4. Location service 178 may use global position system (GPS) data, multilateration, and/or any other known techniques for locating computing devices. Location service 178 may be configured to generate and send a location signal to a robotic device indicating the location of the patient (e.g., the first location) or a location of computing device 12 (e.g., the second location).

Figure 4:
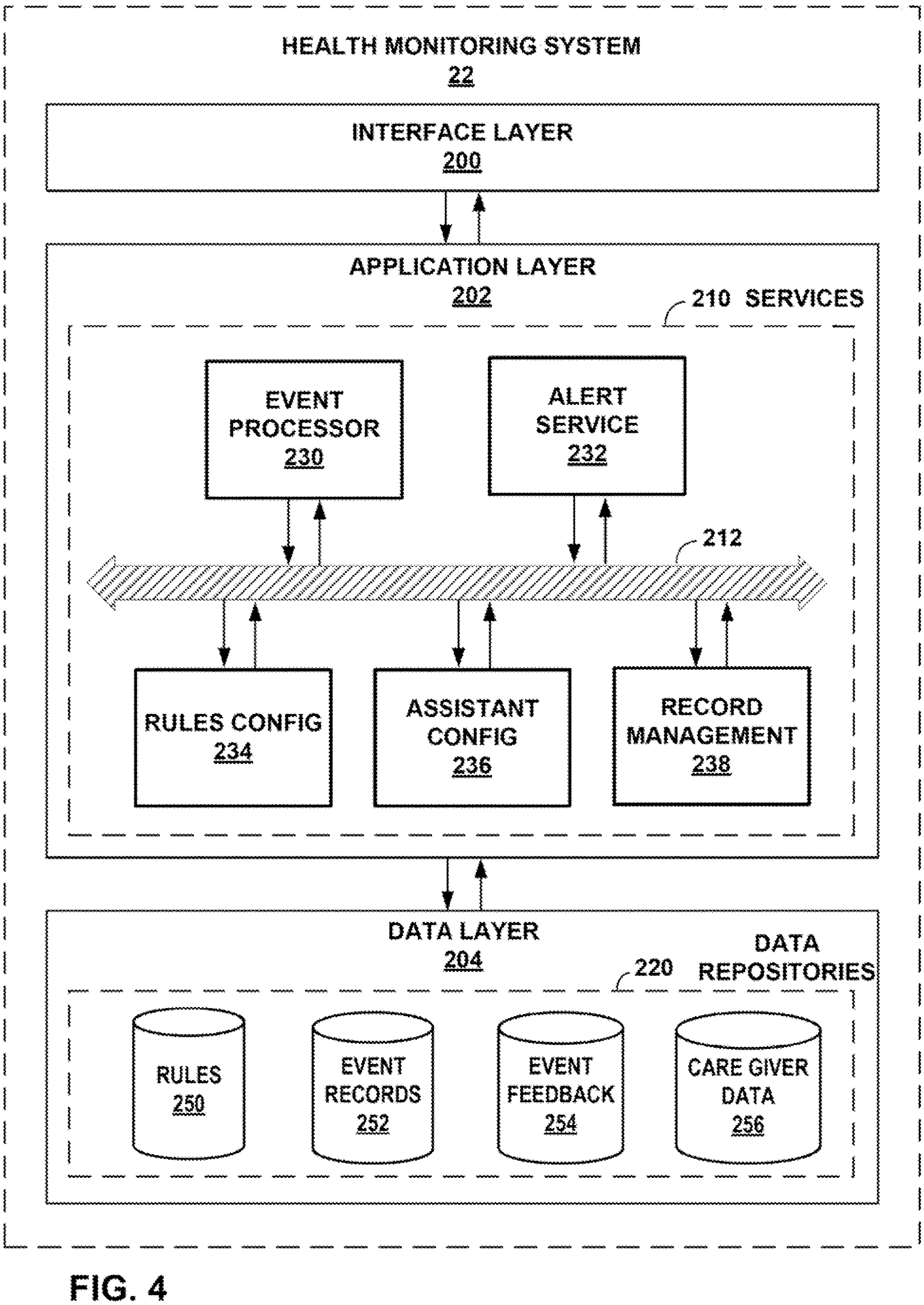
FIG. 4 is a block diagram illustrating an example configuration of a health monitoring system that operates in accordance with one or more techniques of the present disclosure.

FIG. 4 is a block diagram illustrating an operating perspective of HMS 22. HMS 22 may be implemented in a computing system 20, which may include hardware components such as those of computing device 12, embodied in one or more physical devices. FIG. 4 provides an operating perspective of HMS 22 when hosted as a cloud-based platform. In the example of FIG. 4, components of HMS 22 are arranged according to multiple logical layers that implement the techniques of this disclosure. Each layer may be implemented by one or more modules comprised of hardware, software, or a combination of hardware and software.

Computing devices, such as computing devices 12, IoT devices 30, computing devices 38, and computing device 42, operate as clients that communicate with HMS 22 via interface layer 200. For example, HMS 22 may receive physiological data or other information from devices 12, 30, 38, and 42. The computing devices typically execute client software applications, such as desktop application, mobile application, and web applications. Interface layer 200 represents a set of application programming interfaces (API) or protocol interfaces presented and supported by HMS 22 for the client software applications. Interface layer 200 may be implemented with one or more web servers.

As shown in FIG. 4, HMS 22 also includes an application layer 202 that represents a collection of services 210 for implementing the functionality ascribed to HMS herein. Application layer 202 receives information from client applications, e.g., an alert of an acute health event from a computing device 12 or IoT device 30, and further processes the information according to one or more of the services 210 to respond to the information. Application layer 202 may be implemented as one or more discrete software services 210 executing on one or more application servers, e.g., physical or virtual machines. That is, the application servers provide runtime environments for execution of services 210. In some examples, the functionality interface layer 200 as described above and the functionality of application layer 202 may be implemented at the same server. Services 210 may communicate via a logical service bus 212. Service bus 212 generally represents a logical interconnections or set of interfaces that allows different services 210 to send messages to other services, such as by a publish/subscription communication model.

Data layer 204 of HMS 22 provides persistence for information in PPEMS 6 using one or more data repositories 220. A data repository 220, generally, may be any data structure or software that stores and/or manages data. Examples of data repositories 220 include but are not limited to relational databases, multi-dimensional databases, maps, and hash tables, to name only a few examples.

As shown in FIG. 4, each of services 230-238 is implemented in a modular form within HMS 22. Although shown as separate modules for each service, in some examples the functionality of two or more services may be combined into a single module or component. Each of services 230-238 may be implemented in software, hardware, or a combination of hardware and software. Moreover, services 230-238 may be implemented as standalone devices, separate virtual machines or containers, processes, threads, or software instructions generally for execution on one or more physical processors.

Event processor service 230 may be responsive to receipt of an alert transmission from computing device(s) 12 and/or IoT device(s) 30 indicating that IMD 10 detected an acute health event of patient and, in some examples, that the transmitting device confirmed the detection. Event processor service 230 may initiate performance of any of the operations in response to detection of an acute health event ascribed herein to HMS 22, such as communicating with patient 4, bystander 26, and care providers 40, activating robotic device 46 and, in some cases, analyzing data to confirm or override the detection of the acute health event by IMD 10.

Record management service 238 may store the patient data included in a received alert message within event records 252. Alert service 232 may package the some or all of the data from the event record, in some cases with additional information as described herein, into one more alert messages for transmission to bystander 26 and/or care providers 40. Alert service 232 may be configured to send an alert to a robotic device based on physiological data or an instruction received from a medical device. Care giver data 256 may store data used by alert service 232 to identify to whom to send alerts based on locations of potential bystanders 26 and care givers 40 relative to a location of patient 4 and/or applicability of the care provided by care givers 40 to the acute health event experienced by patient 4.

In examples in which HMS 22 performs an analysis to confirm or override the detection of the acute health event by IMD 10, event processor service 230 may apply one or more rules 250 to the data received in the alert message, e.g., to feature vectors derived by event processor service 230 from the data. Rules 250 may include one or more models, algorithms, decision trees, and/or thresholds, which may be developed by rules configuration service 234 based on machine learning. Example machine learning techniques that may be employed to generate rules 250 can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks, Convolution Neural Networks (CNN), Long Short Term Networks (LSTM), the Apriori algorithm, K-Means Clustering, k-Nearest Neighbour (kNN), Learning Vector Quantization (LVQ), Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR).

In some examples, in addition to rules used by HMS 22 to make or confirm an acute health event detection, (or in examples in which HMS 22 does not confirm event detection) rules 250 maintained by HMS 22 may include rules 196 utilized by computing devices 12 and rules 84 used by IMD 10. In such examples, rules configuration service 250 may be configured to develop and maintain rules 196 and rules 84. Rules configuration service 234 may be configured to modify these rules based on event feedback data 254 that indicates whether the detections and confirmations of acute health events by IMD 10, computing device 12, and/or HMS 22 were accurate. Event feedback 254 may be received from patient 4, e.g., via computing device(s) 12, or from care providers 40 and/or EHR 24. In some examples, rules configuration service 234 may utilize event records from true and false detections (as indicated by event feedback data 254) and confirmations for supervised machine learning to further train models included as part of rules 250. In response to determining that an acute health event has occurred or is occurring, HMS 22 may be configured to contact a robotic device with instructions to check on the patient or to administer medical treatment to the patient. Additionally or alternatively, HMS 22 may be configured to contact a neighborhood group and/or emergency medical services in response to determining that an acute health event has occurred or is occurring.

As illustrated in the example of FIG. 4, services 210 may also include an assistant configuration service 236 for configuring and interacting with event assistant 176 implemented in computing device 12 or other computing devices.

Figure 5:
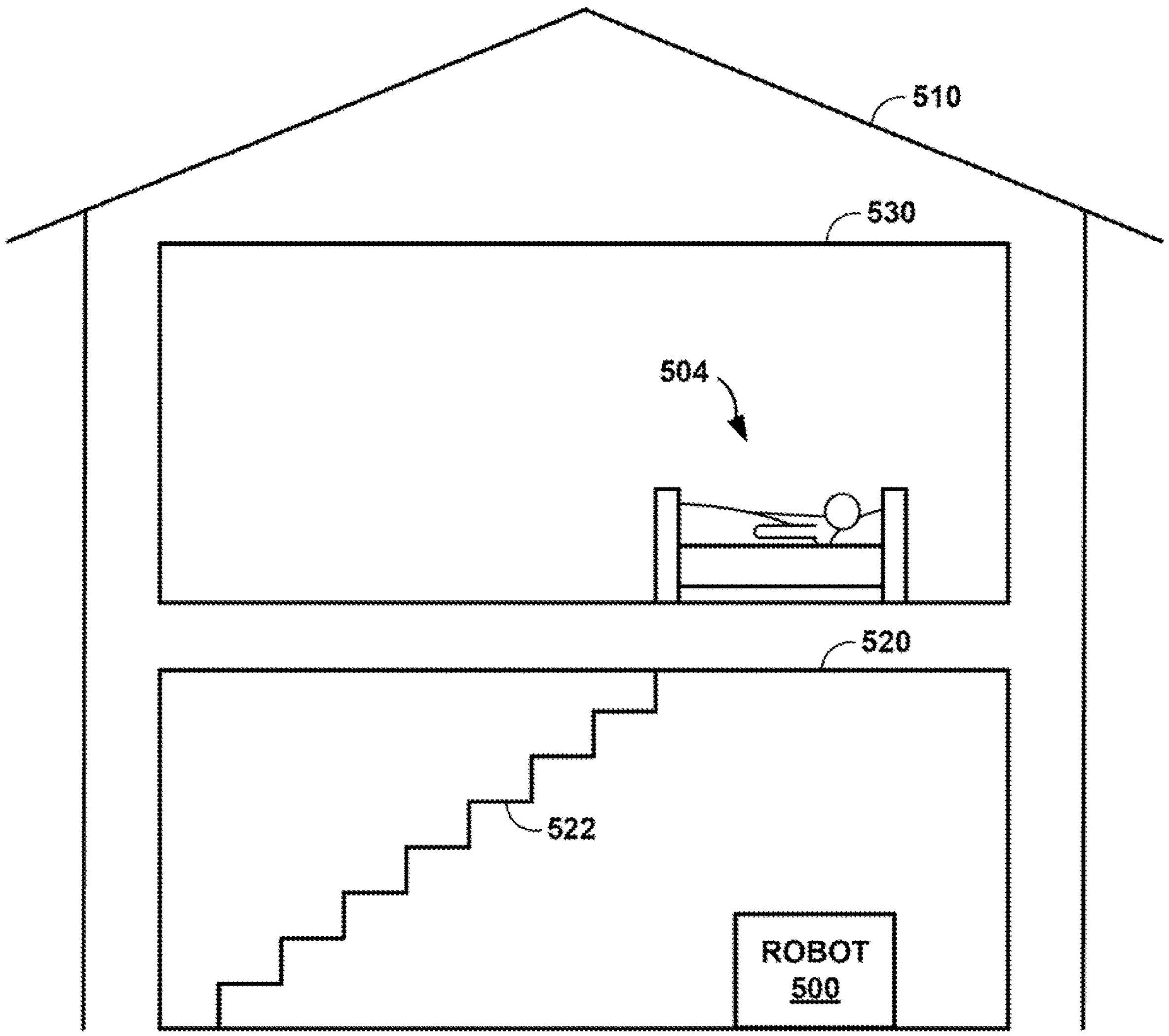
FIG. 5 is a block diagram conceptually illustrating a patient and a robotic device in a residence in accordance with one or more techniques of the present disclosure.

FIG. 5 is a block diagram conceptually illustrating a patient 504 and a robotic device 500 in a residence 510 in accordance with one or more techniques of the present disclosure. Residence 510 includes first floor 520, second floor 530, and stairs 522 between floors 520 and 530. In the example shown in FIG. 5, robotic device 500 is located on first floor 520, and patient 504 is located on second floor 530. Robotic device 500 may be used to confirm that an acute health event has occurred in a single-story residence, in a residence with more than two floors, or in an outdoor setting.

As one hypothetical example, patient 504 experiences an acute health event while sleeping on second floor 530. The acute health event may include a reduction or cessation in breathing or cardiac function. A medical device attached to or proximate to patient 504, e.g., IMD 10, can sense the physiological signal(s) from patient 504 and optionally determine whether patient 504 is experiencing an acute health event. Additionally or alternatively, the medical device can transmit the physiological signal(s) or data to a wearable device or to an external computing device (e.g., computing device(s) 12, IoT device(s) 30, or robotic device 500) for determination of whether patient 504 is experiencing an acute health event. For example, the medical device can transmit physiological data to robotic device 500, which may be configured to determine whether an acute health event has occurred. The medical device may be configured to communicate with robotic device 500 via a direct wireless connection (e.g., Bluetooth), and indirect wireless connection (e.g., Wi-Fi, cellular, and/or Bluetooth through an intermediate device), a wired connection, or any other means of connection.

Additionally or alternatively, the medical device can send information to a remote server for determination of whether a medical event has occurred. Regardless of which entity makes the determination of whether a medical event has occurred, robotic device 500 or another device can contact emergency medical services. Upon activation of a critical alert, while emergency medical services is being contacted, robotic device 500 may be configured to survey the area inside or outside of residence 510 and identify a nearby person to come and perform CPR before emergency medical services arrives.

Robotic device 500 can be housed in a secure charging port with access to the inside or exterior of residence 510. Upon activation, robotic device 500 may search the nearby area and find someone nearby using various recognition methods (sound, visual/image processing, infrared, digital footprint scanning, etc.). Robotic device 500 may be configured to fly to the nearest person and indicate via alerts that help is needed. Robotic device 500 may be configured to guide a bystander who is outside of residence 510 back to residence 510. Robotic device 500 may be configured to provide instructions so that care (CPR, AED, injections, medications) can be performed while EMS arrives. Robotic device 500 may be configured to determine if a bystander has the ability to help, and robotic device 500 may be configured to find a second bystander if the first bystander is unable to help patient 504 without assistance.

In response to a determination that an acute health event has occurred, robotic device 500 may be configured to move to a location proximate patient 504 (e.g., having a direct line of sight to patient 504 or within reach of patient 504). For example, robotic device 500 may be configured to move to a location on second floor 530 where robotic device 500 can take a photograph of patient 504 and/or where robotic device 500 can sense physiological signals from patient 504. Robotic device 500 may be configured to climb stairs 522 and/or fly from first floor 520 to second floor 530. Robotic device 500 may be configured to also open doors or maneuver around or through obstacles. Robotic device 500 may be configured to follow a signal emitted by patient 504, by a medical device on or near patient 504 (e.g., IMD 10), and/or by a computing device 12 of patient 504 (e.g., a mobile phone or tablet of patient 504), such as an audible signal, an electromagnetic signal, or heat generated by patient 504. Although FIG. 5 depicts patient 504 as on second floor 530, patient 504 may instead be on first floor 520 or outside of residence 510 when a medical event occurs.

Robotic device 500 may include sensors for autonomous movement, such as radar, lidar, ultrasound, camera(s), and/or thermal sensor(s). Robotic device 500 may be configured to sense one or more physiological parameters of patient 504 by capturing a photograph, taking a temperature, and/or listening to the pulse or breathing of patient 504. Robotic device 500 may be configured to output voice communication through a speaker and listen for a response from patient 504. In some examples, robotic device 500 may be configured to implement an event assistant to provide a conversation interface with patient 504 or a bystander 26, as described herein. Based on the sensed signals, including any voice communication received from patient 504, robotic device 500 may be configured to determine whether patient 504 is experiencing or has experienced an acute health event.

For example, robotic device 500 may be configured to determine a medical treatment to administer to patient 504 based on a cohort analysis using a current disease state and/or physiological signals of patient 504. Robotic device 500 may be configured to determine that the body temperature of patient 504 should be increased or decreased. Robotic device 500 may be configured to determine that patient 504 is in danger from a specific hazard, such as fire, drowning (e.g., in a bathtub), or an electrical shock (e.g., from an exposed wire). Robotic device 500 may be configured to determine that patient 504 has suffered an injury to the head or neck of patient 504. Robotic device 500 may be configured to determine that patient 504 is in a state of shock.

In response to determining that patient 504 is experiencing or has experienced an acute health event, robotic device 500 may be configured to contact another person by emitting an audible signal (e.g., an alarm or voice command) to alert the other person to come to patient 504. Robotic device 500 may be configured to find a bystander or passer-by using a camera or another sensor and instruct this person to administer medical treatment to patient 504.

Additionally or alternatively, robotic device 500 may be configured to send an alert to a neighborhood group or an emergency medical services provider. For example, robotic device 500 may be able to post a message to a social media platform with information on the location of patient 504 and the acute health event. Robotic device 500 may be configured to open or unlock a door or open a garage door in response to determining that emergency medical services has been contacted or that another person has been instructed to come to the aid of patient 504.

In response to determining that another person has arrived at residence 510, robotic device 500 may be configured to communicate with the other person by, for example, instructing the other person to administer medication or other treatment to patient 504. Robotic device 500 may be configured to provide step-by-step instructions for administering medical treatment to patient 504. Robotic device 500 may provide medication, a syringe, or an AED to the other person to administer to patient 504. Robotic device 500 may also provide a CPR device and/or CPR coaching to the person. Robotic device 504 may be configured to access and ventilate an airway of patient 504.

Robotic device 500 may be configured to administer medical treatment to patient 504 based on the specific medical issue being experienced by patient 504. For example, robotic device 500 may be configured to turn off bath water or shower water to prevent drowning, prevent slipping and falling, or maintain a temperature of patient 504. Robotic device 500 may be configured to move patient to a safer location by pushing, pulling, lifting, or instructing patient 504 to move. For example, robotic device 500 can determine that patient 504 is in an unsafe environment such as an overflowing bathtub, a fire, an electrical hazard, a cold location, or a hot location. Robotic device 500 may be configured to elevate the feet of patient 504 or to stabilize the head or neck of patient 504 in response to that a specific event has occurred. Robotic device 500 may be configured to generate heat or apply cooling in response to determining that a temperature of patient 504 is unacceptably high or low.

Figure 6:
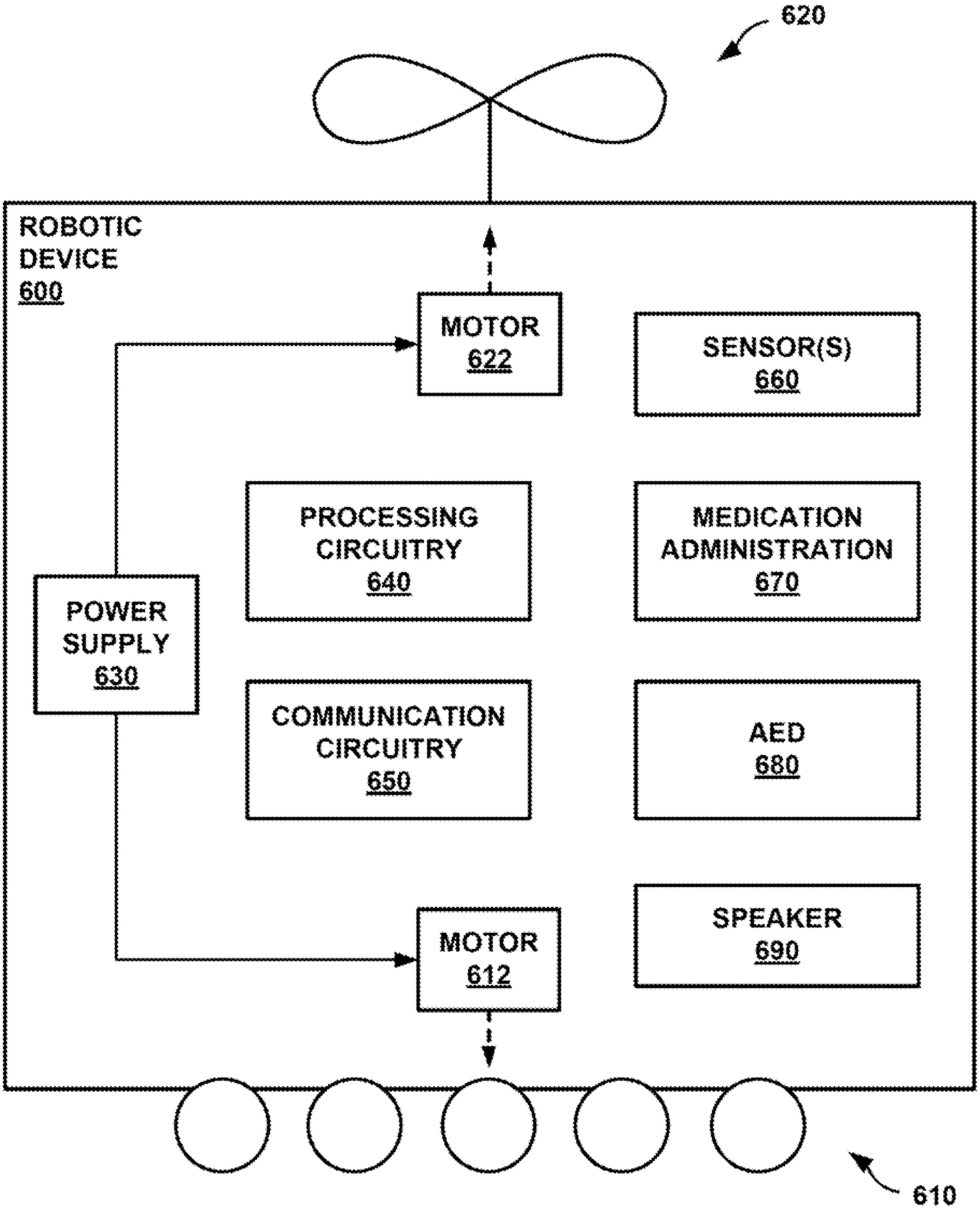
FIG. 6 is a block diagram conceptually illustrating an example robotic device in accordance with one or more techniques of the present disclosure.

FIG. 6 is a block diagram conceptually illustrating an example robotic device 600 in accordance with one or more techniques of the present disclosure. Robotic device 600 may be one example of robotic device 500 in FIG. 5, and robotic device 600 may include a drone, a UAV, a ground-based robot, and/or a marine-based robot. Robotic device 600 includes motors 612 and 622 for driving wheels 610 and propeller 620. In some examples, robotic device 600 may include only a means for moving along the ground (e.g., wheels 610) or a means for flying (e.g., propeller 620). Processing circuitry 640 may be configured to control motors 612 and/or 622 to cause robotic device 600 to move closer to a patient to move back to a base location (e.g., a recharging station). Power supply 630 may include a rechargeable battery that provides power to motors 612 and 622, circuitry 640 and 650, sensor(s) 660, medication administration 670, AED 680, and/or speaker 690. Any of the components shown in FIG. 6 to be inside of robotic device 600 may be external, removable, and/or detachable components.

Processing circuitry 640 may be configured to determine whether an acute health event has occurred or is occurring based on signals received from communication circuitry 650 and/or sensor(s) 660. Robotic device 600 may use sensor(s) 660 to locate or find the patient and/or another person. Processing circuitry 640 may be configured to administer medical treatment via medication administration 670 and/or AED 680. Communication circuitry 650 may be configured to communicate using Bluetooth, Wi-Fi, cellular, ethernet, etc. Sensor(s) 660 may include a camera, a thermometer, a microphone, a thermal sensor, a tactile sensor, and/or any other physiological sensor. Medication administration 670 may be configured to provide medication such as epinephrine, amiodarone, lidocaine, or another medication to address a specific medical issue of the patient. AED 680 may be built into or removable from robotic device 600, so that robotic device 600 can apply AED 680 or another person can apply AED 680.

Figure 7:
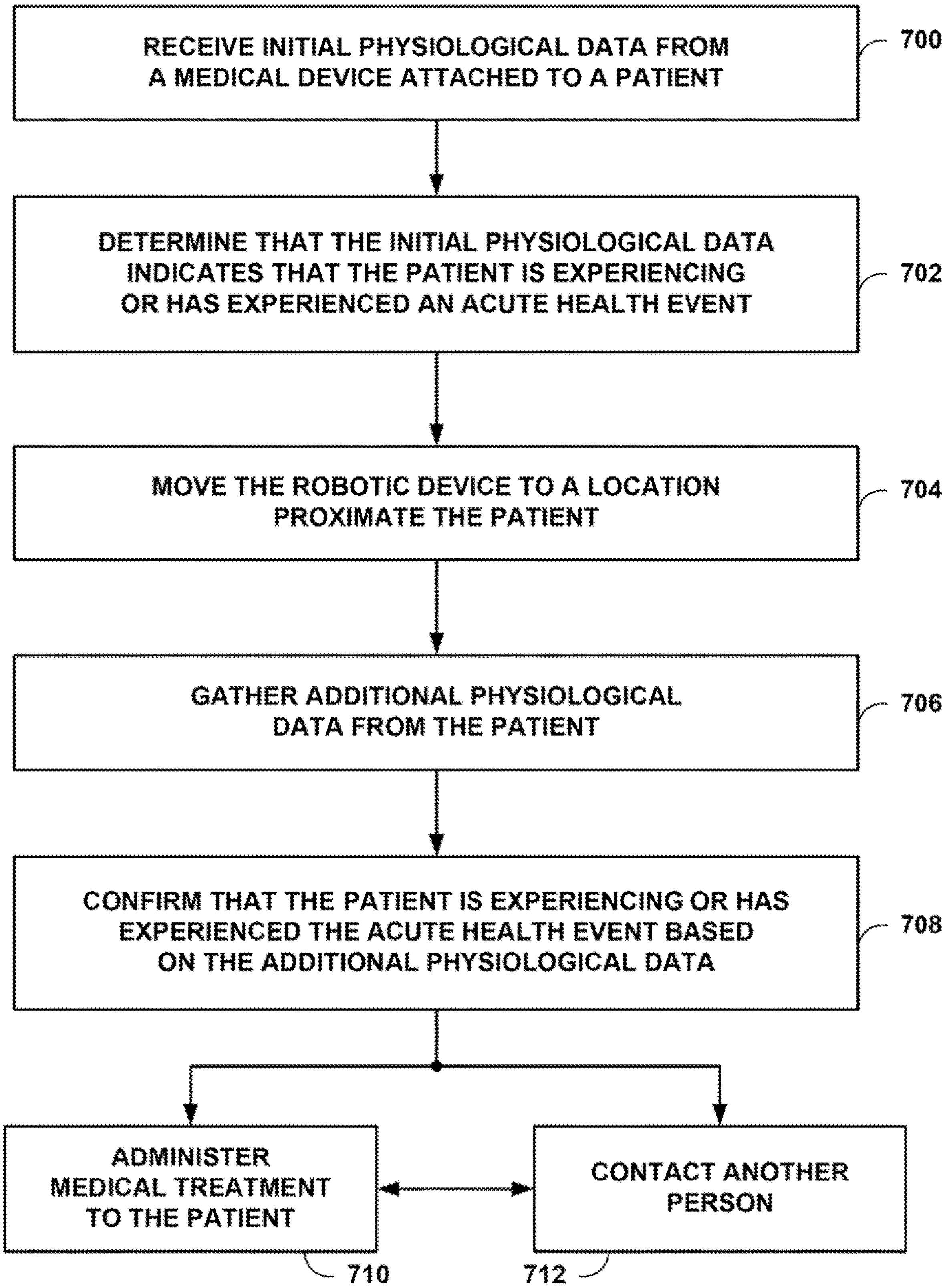
FIG. 7 is a flow diagram illustrating an example technique for providing alerts in response to detection of an acute health event of a patient.

FIG. 7 is a flow diagram illustrating an example technique for providing alerts in response to detection of an acute health event of a patient. The example technique of FIG. 7 is described as being implemented by robotic device 600. In some examples, computing device(s) 12, computing system 20, HMS 22, and/or robotic device 500 may be capable of performing some or all of the functions of the example technique.

According to the example illustrated by FIG. 7, robotic device 600 optionally receives initial physiological data from a medical device attached to a patient (700). The initial physiological data may include data representing cardiac signals, e.g., indicating heart rate, heart rate variability, or morphological features of the cardiac signals, respiration, temperature, or movement of the patient. Additionally or alternatively, the initial physiological data may include an indication of an acute health event experienced by the patient as detected by another device, e.g., IMD 10 and/or computing device(s) 12.

The physiological data received by robotic device 600 may include an instruction message from a medical device or computing device based on the detection of the acute health event by the medical device. The medical device or computing device may generate the instruction message based on physiological data gathered from the patient. The instruction message may direct robotic device 600 to travel to the patient and gather additional physiological data.

Processing circuitry 640 determines that the initial physiological data indicates that the patient is experiencing or has experienced an acute health event (702). Processing circuitry 640 may be configured to compare the physiological data to rules as described above, e.g., a threshold level, to determine whether the physiological data satisfies the rules. In response to determining that the physiological data satisfies the rules, and therefore does not fall with an acceptable, normal, or healthy range, processing circuitry may be configured to determine that the patient is experiencing or has experienced an acute health event. In response to determining that there is no medical event, processing circuitry 640 may be configured to wait for additional physiological data from the patient.

Based on determining that the initial physiological data indicates a medical event, processing circuitry 640 causes motor 612 and/or 622 to move robotic device 600 to a location proximate the patient (704). Processing circuitry 640 can operate a motor to cause a propeller or wheels to move, roll, climb, fly, and/or hover robotic device 600 to a location closer to the patient. Processing circuitry 640 may be configured to determine whether robotic device 600 is within a line of sight of the patient or close enough to the patient in order to determine whether robotic device 600 is proximate the patient.

Sensor(s) 660 gathers additional physiological data from the patient (706). Processing circuitry 640 may be configured to cause sensor(s) 660 to take an image of the patient, such as an image of the face of the patient, to confirm whether the patient is conscious or having a seizure or stroke. Processing circuitry 640 may be configured to cause sensor(s) 660 to perform other forms of imaging such as infrared imaging to discern blood flow. Additionally or alternatively, processing circuitry 640 may be configured to cause sensor(s) 660 to perform depth sensing to determine breathing. Robotic device 600 may be configured to place one or more of sensor(s) 660 on patient 604. Sensor(s) 660 may be able to measure the ECG, pulse, heart rate, respiration, and/or temperature of the patient. Sensor(s) 660 may include a microphone for detecting the speech, heart sounds, or breathing of the patient. Sensor(s) 660 may include a tactile sensor or means for applying to pressure to the patient to wake up the patient.

Processing circuitry 640 confirms that the patient is experiencing or has experienced the acute health event based on the additional physiological data (708). Processing circuitry 640 may be configured to compare the physiological data to a threshold level to determine whether the physiological data satisfies the threshold level.

Additionally or alternatively, processing circuitry 640 may be configured to perform image processing on a photograph captured by sensor(s) 660 to determine whether the patient is conscious. In response to determining that the physiological data does not fall with an acceptable, normal, or healthy range, processing circuitry may be configured to confirm that the patient is experiencing or has experienced an acute health event.

Medication administration 670 or AED 680 administers medical treatment to the patient (710). For example, processing circuitry 640 may be configured to cause medication administration 670 to inject the patient with a needle to deliver epinephrine, amiodarone, lidocaine, or another medication in response to determining that the patient is having an allergic reaction to food or an animal. Additionally or alternatively, processing circuitry 640 may be configured to cause AED 680 to shock the patient. Robotic device 600 may be able to move close enough to the patient to place electrodes on part(s) of the patient before delivering the electrical shock.

Processing circuitry 640 contacts another person (712), either through communication circuitry 650 and/or speaker 690. For example, processing circuitry 640 may be configured to cause speaker 690 to issue an audible alert to anyone nearby. Robotic device 600 may search for a bystander or passer-by and instruct this person to give aid to the patient. Robotic device 600 may provide instructions to this person to place a sensor or an electrode on the patient or to administer medication to the patient. Additionally or alternatively, processing circuitry 640 may be configured to contact a neighborhood group, such as a local social media group, via an internet connection. Processing circuitry 640 may be configured to contact emergency medical services to report the acute health event.

Figure 8:
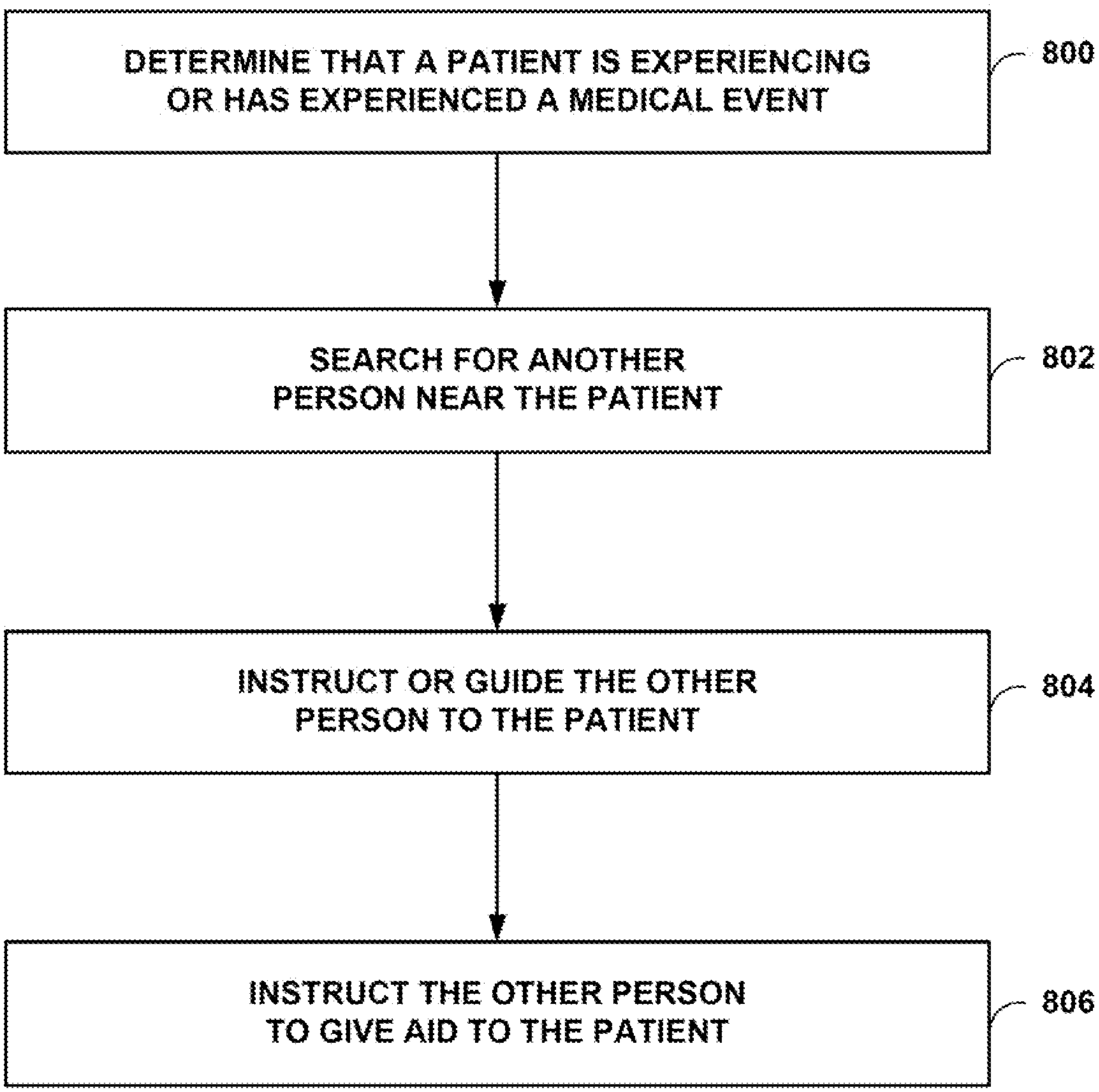
FIG. 8 is a flow diagram illustrating an example technique for contacting another person in response to detection of an acute health event of a patient.

FIG. 8 is a flow diagram illustrating an example technique for contacting another person in response to detection of an acute health event of a patient. The example technique of FIG. 8 is described as being implemented by robotic device 600. In some examples, computing device(s) 12, computing system 20, and/or robotic device 500 may be capable of performing some or all of the functions of the example technique.

In the example of FIG. 8, robotic device 600 determines that a patient is experiencing or has experienced a medical event (800). Robotic device 600 then searches for another person near the patient (802). In some examples, robotic device 600 may be configured to determine whether there is another person at a location close enough to witness the medical event before contacting another person. Thus, robotic device 600 may determine whether the medical event is unwitnessed. In response to determining that the medical event is unwitnessed, robotic device 600 may be configured to emit an audible alert informing another nearby of the medical event. If no one responds to the audible alert, robotic device 600 may begin searching for another person at a farther distance from the patient.

After finding the other person, robotic device 600 may be configured to instruct or guide the other person to the patient (804). Robotic device 600 may be configured to instruct the other person to follow robotic device 600 as robotic device 600 travels back to the patient. In the example of FIG. 8, robotic device 600 then instructs the other person to give aid to the patient (806). The instructions may be for defibrillation, CPR, an injection, and/or for checking a physiological parameter of the patient.

Robotic device 600 may be configured to record video and/or audio throughout the medical event and medical treatment process. Robotic device 600 may be configured to transmit a video or audio feed to the dispatcher for emergency medical services. The dispatcher may be able to connect with robotic device 600 so that emergency medical services can be in contact with a bystander over audio and video. The dispatcher may relay instructions on how to enter the home (e.g., garage code, door code, or key placement). The dispatcher could also tell the bystander the exact location of the patient, as well as the medical condition of the patient or any special considerations. Robotic device 600 may be configured to track the timing of the medical event to bystander interaction, along with the location of bystander(s) for future deployments to save time.

Example 1. A method comprising: determining, by processing circuitry of the robotic device, that a patient is experiencing or has experienced an acute health event; moving the robotic device to a location proximate the patient in response to determining that the patient is experiencing or has experienced the acute health event; gathering, by a sensor of the robotic device, physiological data from the patient after moving the robotic device to the location proximate the patient; confirming, by the processing circuitry, that the patient is experiencing or has experienced the acute health event based on the additional physiological data; and generating an output in response to confirming that the patient is experiencing or has experienced the acute health event.

Example 2. The method of Example 1, further comprising receiving a message from a medical device attached to the patient.

Example 3. The method of Example 2, wherein receiving the message comprises receiving the message from the medical device via a Bluetooth connection between the medical device and the robotic device.

Example 4. The method of Example 2 or Example 3, wherein the message received from the medical device includes initial physiological data.

Example 5. The method of Example 4, wherein determining that the patient is experiencing or has experienced an acute health event is based on the initial physiological data.

Example 6. The method of the preceding Examples or any combination thereof, wherein receiving the initial physiological data comprises receiving the initial physiological data via a computing device communicatively coupled with the medical device.

Example 7. The method of Example 6, wherein the computing device comprises a mobile phone or a tablet.

Example 8. The method of Example 6, wherein the computing device comprises a wearable device, a watch, a ring, a bracelet, a necklace, an anklet, a belt, an article of clothing, or an IoT device.

Example 9. The method of the preceding Examples or any combination thereof, wherein the location is a first location, the method further comprising determining a second location of a mobile phone before moving the robotic device to the first location proximate the patient.

Example 10. The method of the preceding Examples or any combination thereof, wherein the location is a first location, the method further comprising determining a second location of the patient based on a signal from the medical device before moving the robotic device to the first location proximate the patient.

Example 11. The method of the preceding Examples or any combination thereof, wherein the location is a first location, the method further comprising determining a second location of the patient based on thermal sensing before moving the robotic device to the first location proximate the patient.

Example 12. The method of the preceding Examples or any combination thereof, wherein moving the robotic device comprises moving the robotic device to the location where the patient is within a direct line of sight of the robotic device.

Example 13. The method of the preceding Examples or any combination thereof, wherein moving the robotic device comprises moving the robotic device to the location where the robotic device can place the sensor on the patient.

Example 14. The method of the preceding Examples or any combination thereof, wherein gathering the additional physiological data comprises capturing an image of the patient.

Example 15. The method of the preceding Examples or any combination thereof, wherein gathering the additional physiological data comprises capturing an image of a face of the patient.

Example 16. The method of the preceding Examples or any combination thereof, wherein gathering the additional physiological data comprises sensing an electrocardiogram of the patient.

Example 17. The method of the preceding Examples or any combination thereof, wherein gathering the additional physiological data comprises sensing respiration of the patient.

Example 18. The method of the preceding Examples or any combination thereof, wherein gathering the additional physiological data comprises: communicating audibly with the patient; and listening for an audible reply from the patient.

Example 19. The method of the preceding Examples or any combination thereof, wherein gathering the additional physiological data comprises sensing a heart rate of the patient.

Example 20. The method of the preceding Examples or any combination thereof, wherein gathering the additional physiological data comprises tactile sensing.

Example 21. The method of the preceding Examples or any combination thereof, wherein the robotic device comprises a defibrillator, and wherein generating the output comprises administering, by the robotic device, defibrillation to the patient using the defibrillator.

Example 22. The method of the preceding Examples or any combination thereof, wherein generating the output comprises administering, by the robotic device, a direct shock to the patient.

Example 23. The method of the preceding Examples or any combination thereof, wherein the robotic device comprises a cardiopulmonary resuscitation (CPR) machine, and wherein generating the output comprises performing CPR on the patient using the CPR machine.

Example 24. The method of the preceding Examples or any combination thereof, wherein generating the output comprises administering medication to the patient.

Example 25. The method of Example 24, wherein administering the medication comprises injecting epinephrine, amiodarone, or lidocaine in the patient.

Example 26. The method of the preceding Examples or any combination thereof, wherein generating the output comprises accessing an airway of the patient and ventilating the airway.

Example 27. The method of the preceding Examples or any combination thereof, wherein generating the output comprises turning off a water faucet.

Example 28. The method of the preceding Examples or any combination thereof, wherein generating the output comprises moving the patient away from a bathtub, a fire, or an electrical hazard.

Example 29. The method of the preceding Examples or any combination thereof, further comprising determining a medical treatment based on cohort analysis of a disease state of the patient, wherein generating the output comprises administering the medical treatment.

Example 30. The method of the preceding Examples or any combination thereof, further comprising determining a medical treatment based on cohort analysis of a disease state of the patient, wherein generating the output comprises instructing another person to administer the medical treatment.

Example 31. The method of the preceding Examples or any combination thereof, wherein generating the output comprises administering intravenous fluids.

Example 32. The method of the preceding Examples or any combination thereof, wherein generating the output comprises placing a cooling blanket, an ice pack, or a cooling pad on the patient.

Example 33. The method of the preceding Examples or any combination thereof, wherein generating the output comprises elevating feet of the patient above a head of the patient.

Example 34. The method of the preceding Examples or any combination thereof, wherein generating the output comprises elevating feet of the patient above a chest of the patient.

Example 35. The method of the preceding Examples or any combination thereof, wherein generating the output comprises stabilizing a head of the patient.

Example 36. The method of the preceding Examples or any combination thereof, wherein generating the output comprises unlocking a door, opening a door, or opening a garage door.

Example 37. The method of the preceding Examples or any combination thereof, wherein generating the output comprises generating an audible alert.

Example 38. The method of the preceding Examples or any combination thereof, wherein generating the output comprises instructing another person to go to a location of the patient.

Example 39. The method of the preceding Examples or any combination thereof, wherein generating the output comprises instructing another person to administer medical treatment to the patient.

Example 40. The method of the preceding Examples or any combination thereof, further comprising determining a medical treatment based on cohort analysis of a disease state of the patient, wherein generating the output comprises instructing another person to administer the medical treatment.

Example 41. The method of the preceding Examples or any combination thereof, wherein generating the output comprises instructing another person to perform cardiopulmonary resuscitation on the patient.

Example 42. The method of the preceding Examples or any combination thereof, wherein generating the output comprises transmitting a message to a social media group.

Example 43. The method of the preceding Examples or any combination thereof, wherein generating the output comprises transmitting a message to a neighborhood group.

Example 44. The method of the preceding Examples or any combination thereof, wherein generating the output comprises contacting a caregiver for the patient.

Example 45. The method of the preceding Examples or any combination thereof, wherein generating the output comprises contacting an emergency medical system.

Example 46. The method of the preceding Examples or any combination thereof, wherein the medical device is implanted in the patient.

Example 47. The method of the preceding Examples or any combination thereof, wherein the medical device comprises a wearable device attached to the patient.

Example 48. A robotic device comprising: processing circuitry configured to determine whether a patient is experiencing or has experienced an acute health event; a motor configured to move the robotic device to a location proximate the patient; and a sensor configured to gather physiological data from the patient, wherein processing circuitry is further configured to: confirm whether the patient is experiencing or has experienced the acute health event based on the physiological data; and generate an output in response to confirming that the patient is experiencing or has experienced the acute health event.

Example 49. The robotic device of Example 48, wherein the communication circuitry, processing circuitry, and sensor are configured to perform the method of Examples 1-47 or any combination thereof.

Example 50. A system comprising: means for determining that a patient is experiencing or has experienced an acute health event; means for moving a robotic device to a location proximate the patient; means for gathering physiological data from the patient; means for confirming that the patient is experiencing or has experienced the acute health event based on the physiological data; and means for generating an output in response to confirming that the patient is experiencing or has experienced the acute health event.

Example 51. The system of Example 50, further comprising means for performing the method of Examples 1-47 or any combination thereof.

Example 52. A device comprising a computer-readable medium having executable instructions stored thereon, configured to be executable by processing circuitry for causing the processing circuitry to: determine that a patient is experiencing or has experienced an acute health event; cause a motor to move a robotic device to a location proximate the patient; cause a sensor of the robotic device to gather physiological data from the patient; confirm that the patient is experiencing or has experienced the acute health event based on the physiological data; and generate an output in response to confirming that the patient is experiencing or has experienced the acute health event.

Example 53. The device of Example 52, wherein the instructions are configured to be executable by the processing circuitry for further causing the processing circuitry to perform the method of Examples 1-47 or any combination thereof.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

Various examples have been described. These and other examples are within the scope of the following Examples.

What is claimed is:

1. A method comprising:

determining, by processing circuitry of a robotic device, that a patient is experiencing or has experienced an acute health event, wherein the acute health event comprises at least one of a cardiac arrest, a ventricular fibrillation, a ventricular tachycardia, a myocardial infarction, asystole, Pulseless Electrical Activity (PEA), acute respiratory distress syndrome (ARDS), or a seizure;

moving the robotic device to a location proximate the patient in response to determining that the patient is experiencing or has experienced the acute health event;

gathering, by a sensor of the robotic device, physiological data from the patient after moving the robotic device to the location proximate the patient;

confirming, by the processing circuitry, that the patient is experiencing or has experienced the acute health event based on the gathered physiological data; and generating an output in response to confirming that the patient is experiencing or has experienced the acute health event.

2. The method of claim 1, further comprising receiving a message from a medical device attached to the patient.

3. The method of claim 2, wherein receiving the message comprises receiving the message from the medical device via a Bluetooth connection between the medical device and the robotic device.

4. The method of claim 3, wherein the message received from the medical device includes initial physiological data.

5. The method of claim 4, wherein determining that the patient is experiencing or has experienced an acute health event is based on the initial physiological data.

6. The method of claim 4, wherein receiving the initial physiological data comprises receiving the initial physiological data via a computing device communicatively coupled with the medical device.

7. The method of claim 6, wherein the computing device comprises a mobile phone or a tablet.

8. The method of claim 6, wherein the computing device comprises a wearable device, a watch, a ring, a bracelet, a necklace, an anklet, a belt, an article of clothing, or an IoT device.

9. The method of claim 1, wherein the location is a first location, the method further comprising determining a second location of a mobile phone before moving the robotic device to the first location proximate the patient.

10. The method of claim 1, wherein the location is a first location, the method further comprising determining a second location of the patient based on a signal from the medical device before moving the robotic device to the first location proximate the patient.

11. The method of claim 1, the method further comprising determining a location of the patient based on thermal sensing before moving the robotic device to the location proximate the patient.

12. The method of claim 1, wherein moving the robotic device comprises moving the robotic device to a location where the patient is within a direct line of sight of the robotic device.

13. A robotic device comprising:
- processing circuitry configured to determine whether a patient is experiencing or has experienced an acute health event, wherein the acute health event comprises at least one of a cardiac arrest, a ventricular fibrillation, a ventricular tachycardia, a myocardial infarction, asystole, Pulseless Electrical Activity (PEA), acute respiratory distress syndrome (ARDS), or a seizure;
- a motor configured to move the robotic device to a location proximate the patient; and
- a sensor configured to gather physiological data from the patient,
- wherein the processing circuitry is further configured to:
  - confirm whether the patient is experiencing or has experienced the acute health event based on the physiological data; and
  - generate an output in response to confirming that the patient is experiencing or has experienced the acute health event.

14. A system comprising:
- means for determining that a patient is experiencing or has experienced an acute health event, wherein the acute health event comprises at least one of a cardiac arrest, a ventricular fibrillation, a ventricular tachycardia, a myocardial infarction, asystole, Pulseless Electrical Activity (PEA), acute respiratory distress syndrome (ARDS), or a seizure;
- means for moving a robotic device to a location proximate the patient;
- means for gathering physiological data from the patient;
- means for confirming that the patient is experiencing or has experienced the acute health event based on the physiological data; and
- means for generating an output in response to confirming that the patient is experiencing or has experienced the acute health event.

15. A device comprising a computer-readable medium having executable instructions stored thereon, configured to be executable by processing circuitry for causing the processing circuitry to:
- determine that a patient is experiencing or has experienced an acute health event, wherein the acute health event comprises at least one of a cardiac arrest, a ventricular fibrillation, a ventricular tachycardia, a myocardial infarction, asystole, Pulseless Electrical Activity (PEA), acute respiratory distress syndrome (ARDS), or a seizure;
- cause a motor to move a robotic device to a location proximate the patient;
- cause a sensor of the robotic device to gather physiological data from the patient;
- confirm that the patient is experiencing or has experienced the acute health event based on the physiological data; and
- generate an output in response to confirming that the patient is experiencing or has experienced the acute health event.

16. The robotic device of claim 13, wherein the processing circuitry is further configured to:
- receive a message from a medical device attached to the patient, the message including initial physiological data.

17. The robotic device of claim 16, wherein the processing circuitry is further configured to:
- determine that the patient is experiencing or has experienced an acute health event based on the initial physiological data.

18. The robotic device of claim 13, wherein the location is a first location, and the processing circuitry is further configured to:
- determine a second location of a mobile phone before moving the robotic device to the first location proximate the patient.

19. The robotic device of claim 13, wherein the location is a first location, and the processing circuitry is further configured to:
- determine a second location of the patient based on a signal from the medical device before moving the robotic device to the first location proximate the patient.

20. The robotic device of claim 13, wherein the processing circuitry is further configured to:
- determine a location of the patient based on thermal sensing before moving the robotic device to the location proximate the patient.

21. The method of claim 1, wherein determining that the patient is experiencing or has experienced the acute health event comprises:
- receiving, by the processing circuitry, a message from a medical device attached to the patient, wherein the message comprises physiological data;
- comparing, by the processing circuitry, the physiological data to one or more rules; and
- determining, by the processing circuitry, that the physiological data satisfies the one or more rules.

22. The method of claim 1, wherein the sensor of the robotic device comprises at least one of a camera, a thermometer, a microphone, a thermal sensor, a tactile sensor, radar, lidar, or an ultrasound sensor.

23. The method of claim 1, wherein moving the robotic device to the location proximate the patient in response to determining that the patient is experiencing or has experienced the acute health event comprises:

autonomously activating, by the processing circuitry, a motor of the robotic device in response to determining that the patient is experiencing or has experienced the acute health event;

sensing, by the sensor of the robotic device, surroundings of the robotic device; and controlling, by the processing circuitry, the robotic device to navigate around an obstacle based on the sensed surroundings.

24. A method comprising:

receiving, by processing circuitry of a robotic device, a message from a medical device attached to the patient, wherein the message comprises physiological data;

comparing, by the processing circuitry, the physiological data to one or more rules;

determining, by the processing circuitry, that the physiological data satisfies the one or more rules;

responsive to the physiological data satisfying the one or more rules, determining, by the processing circuitry, that a patient is experiencing or has experienced an acute health event;

moving the robotic device to a location proximate the patient in response to determining that the patient is experiencing or has experienced the acute health event;

gathering, by a sensor of the robotic device, physiological data from the patient after moving the robotic device to the location proximate the patient;

confirming, by the processing circuitry, that the patient is experiencing or has experienced the acute health event based on the gathered physiological data; and generating an output in response to confirming that the patient is experiencing or has experienced the acute health event.

* * * * *